US007956172B2

(12) United States Patent
Miyawaki et al.

(10) Patent No.: US 7,956,172 B2
(45) Date of Patent: Jun. 7, 2011

(54) FLUORESCENT PROTEIN AND CHROMOPROTEIN

(75) Inventors: Atsushi Miyawaki, Saitama (JP); Hidekazu Tsutsui, Saitama (JP); Satoshi Karasawa, Tokyo (JP)

(73) Assignees: Riken, Saitama (JP); Medical & Biological Laboratories Co., Ltd, Aichi (JP)

( * ) Notice: Subject to any disclaimer, the term of this patent is extended or adjusted under 35 U.S.C. 154(b) by 1313 days.

(21) Appl. No.: 10/561,041

(22) PCT Filed: Jun. 16, 2004

(86) PCT No.: PCT/JP2004/008786
§ 371 (c)(1),
(2), (4) Date: Jul. 3, 2006

(87) PCT Pub. No.: WO2004/111235
PCT Pub. Date: Dec. 23, 2004

(65) Prior Publication Data
US 2009/0170073 A1    Jul. 2, 2009

(30) Foreign Application Priority Data

Jun. 16, 2003 (JP) ................. 2003-170324
Jun. 16, 2003 (JP) ................. 2003-170325
Jun. 16, 2003 (JP) ................. 2003-170326
Jun. 16, 2003 (JP) ................. 2003-170327
Jun. 16, 2003 (JP) ................. 2003-170328
Jun. 16, 2003 (JP) ................. 2003-170329

(51) Int. Cl.
*C12N 15/12* (2006.01)
(52) U.S. Cl. ..................................... 536/23.5
(58) Field of Classification Search ........................ None
See application file for complete search history.

(56) References Cited

U.S. PATENT DOCUMENTS

| 5,998,204 | A | * | 12/1999 | Tsien et al. | ............ 435/325 |
| 6,627,449 | B1 | * | 9/2003 | Tsien et al. | ............ 436/86 |
| 7,060,869 | B2 | * | 6/2006 | Tsien et al. | ............ 800/18 |
| 7,160,698 | B2 | * | 1/2007 | Matz et al. | ............ 435/69.1 |
| 7,226,993 | B2 | * | 6/2007 | Miyawaki et al. | ............ 530/350 |
| 7,247,449 | B2 | * | 7/2007 | Miyawaki et al. | ............ 435/69.1 |
| 7,345,157 | B2 | * | 3/2008 | Miyawaki et al. | ............ 536/23.1 |
| 7,375,201 | B2 | * | 5/2008 | Miyawaki et al. | ............ 536/23.1 |
| 7,504,491 | B2 | * | 3/2009 | Miyawaki et al. | ............ 536/23.1 |
| 7,541,451 | B2 | * | 6/2009 | Miyawaki et al. | ............ 536/23.1 |
| 7,547,528 | B2 | * | 6/2009 | Miyawaki et al. | ............ 435/69.1 |
| 2004/0110225 | A1 | * | 6/2004 | Gibbs et al. | ............ 435/7.1 |
| 2005/0090642 | A1 | | 4/2005 | Miyawaki et al. | |
| 2005/0106661 | A1 | | 5/2005 | Miyawaki et al. | |
| 2005/0208624 | A1 | * | 9/2005 | Miyawaki et al. | ............ 435/69.1 |
| 2006/0154296 | A1 | | 7/2006 | Miyawaki et al. | |
| 2006/0160990 | A1 | | 7/2006 | Miyawaki et al. | |
| 2006/0240472 | A1 | | 10/2006 | Miyawaki et al. | |

FOREIGN PATENT DOCUMENTS

| JP | 2002-531146 | 9/2002 |
| WO | 00/34318 | 6/2000 |
| WO | 00/34319 | 6/2000 |
| WO | 00/34320 | 6/2000 |
| WO | 00/34321 | 6/2000 |
| WO | 00/34526 | 6/2000 |
| WO | 00/46233 | 8/2000 |
| WO | 01/27150 | 4/2001 |
| WO | 02/068459 | 9/2002 |
| WO | 02/090535 | 11/2002 |
| WO | 02/096924 | 12/2002 |
| WO | 03/033693 | 4/2003 |
| WO | 03/042401 | 5/2003 |
| WO | 03/054191 | 7/2003 |
| WO | 03/104460 | 12/2003 |
| WO | 03/104461 | 12/2003 |
| WO | 2004/018671 | 3/2004 |
| WO | 2004/111236 | 12/2004 |
| WO | 2005/019252 | 3/2005 |
| WO | 2004/054464 | 6/2005 |

OTHER PUBLICATIONS

Karasawa et al. ("Cyan-emitting and orange-emitting fluorescent proteins as a donor/acceptor pair for fluorescence resonance energy transfer." Biochem. J., published Apr. 5, 2004, 381, 307-312).*
Papina et al. ("Separation of highly fluorescent proteins by SDS-PAGE in Acroporidae corals," Comparative Biochemistry and Physiology Part B, 131 (2002) 767-774).*
GenBank: AB128822.1, 2004.*
Weisstein, Eric W. "Combination." From MathWorld—A Wolfram Web Resource. http://mathworld.wolfram.com/Combination.html, downloaded Dec. 16, 2010.*
Verkhusha et al. "The molecular properties and applications of Anthozoa fluorescent proteins and chromoproteins," Nature Biotechnology, 2004, 22, 289-296.*
M. Matz et al., "Fluorescent Proteins from Nonbioluminescent Anthozoa Species", *Nature Biotechnology*, vol. 17, pp. 969-973 (1999).
K. Lukyanov et al., "Natural Animal Coloration Can be Determined by a Nonfluorescent Green Fluorescent Protein Homolog", *The Journal of Biological Chemistry*, vol. 275, No. 34, pp. 25879-25882 (Aug. 25, 2000).
T. Beddoe et al., "The Production, Purification, and Crystallization of a Pocilloporin Pigment from a Reef-forming Coral", *Acta Crystallographica Section D*, vol. 59, No. 3, pp. 597-599 (Mar. 2003).
U.S. Appl. No. 10/492,081 (Miyawaki et al.), filed Oct. 25, 2004 and entitled "Fluorescent Protein".
U.S. Appl. No. 10/498,505 (Miyawaki et al.), filed Nov. 22, 2004 and entitled "Fluorescent Protein".
U.S. Appl. No. 10/525,365 (Miyawaki et al.), filed Oct. 12, 2005 and entitled "Fluorescent Protein and Chromoprotein".

(Continued)

*Primary Examiner* — Christina Bradley
(74) *Attorney, Agent, or Firm* — Greenblum & Bernstein, P.L.C.

(57) ABSTRACT

It is an object of the present invention to provide a novel fluorescent protein and a novel chromoprotein. The present invention provides a novel fluorescent protein derived from *Montipora* sp., *Acropora* sp. and *Lobophytum crassum*, and a novel chromoprotein derived from *Actinia equine*.

4 Claims, 8 Drawing Sheets

OTHER PUBLICATIONS

U.S. Appl. No. 10/581,551 (Miyawaki et al.), filed Jun. 2, 2006 and entitled "Fluorescent Proteins".

U.S. Appl. No. 11/390,215 (Miyawaki et al.), filed Mar. 28, 2006 and entitled "A Method for Analysis of Protein Interaction using Fluorescent Protein".

U.S. Appl. No. 10/561,040 (Miyawaki et al.), filed Dec. 16, 2005 and entitled "Fluorescent Protein".

U.S. Appl. No. 10/516,314 (Miyawaki et al.), filed Dec. 12, 2004 and entitled "Pigment Protein".

U.S. Appl. No. 10/516,317 (Miyawaki et al.), filed Dec. 12, 2004 and entitled "Pigment Protein".

Dove et al., "Isolation and partial characterization of the pink and blue pigments of pocilloporid and acroporid corals" *Biological Bulletin* 189(3):288-297, 1995.

Salih et al. "Fluorescent pigments in corals are photoprotective" *Nature* 408(6814):850-853, 2000.

Extended European Search Report issued with respect to European Application EP 09163975.7, dated Aug. 4, 2009.

* cited by examiner

A

B

A

B

C

A

B

C

A

B

A

B

A

B

FLUORESCENT PROTEIN AND CHROMOPROTEIN

TECHNICAL FIELD

The present invention relates to a novel fluorescent protein. More specifically, the present invention relates to a novel fluorescent protein derived from *Montipora* sp., *Acropora* sp., and *Lobophytum crassum*, and the use thereof.

Further, the present invention relates to a novel chromoprotein. More specifically, the present invention relates to a novel chromoprotein derived from *Actinia equine*, and use thereof.

BACKGROUND ART

Green fluorescent protein (GFP) derived from *Aequorea victoria*, a jellyfish, has many purposes in biological systems. Recently, various GFP mutants have been produced based on the random mutagenesis and semi-rational mutagenesis, wherein a color is changed, a folding property is improved, luminance is enhanced, or pH sensitivity is modified. Fluorescent proteins such as GFP are fused with other proteins by gene recombinant technique, and monitoring of the expression and transportation of the fusion proteins is carried out.

One of the most commonly used types of GFP mutant is Yellow fluorescent protein (YFP). Among *Aequorea*-derived GFP mutants, YFP exhibits the fluorescence with the longest wavelength. The values $\epsilon$ and $\Phi$ of the majority of YEPs are 60,000 to 100,000 $M^{-1}cm^{-1}$ and 0.6 to 0.8, respectively (Tsien, R. Y. (1998). Ann. Rev. Biochem. 67, 509-544). These values are comparable to those of the general fluorescent group (fluorescein, rhodamine, etc.). Accordingly, improvement of the absolute luminance of YFP is nearly approaching its limit.

In addition, cyan fluorescent protein (CFP) is another example of the GFP mutant. Of this type of protein, ECFP (enhanced cyan fluorescent protein) has been known. Moreover, red fluorescent protein (RFP) has been isolated from sea anemone (*Discoma* sp.). Of this type of protein, DasRed has been known. Thus, 4 types of fluorescent proteins, that are, green fluorescent protein, yellow fluorescent protein, cyan fluorescent protein, and red fluorescent protein, have successively been developed. The range of the spectrum has significantly been expanded.

In addition, some cnidarians emit a fluorescence. The cloning of fluorescent protein genes derived from such cnidarians has been attempted. However, in order to expand the repertoire of fluorescent and biochemical properties, it is necessary to clone more genes.

On the other hand, a chromoprotein is obtained by bringing close to 0 (zero) the quantum yield of a conventional fluorescent protein. Such a chromoprotein can be applied to various purposes because it is able to introduce into a cell a molecule for converting light energy to other types of energy. However, there have been only a few reports regarding the absorption wavelength properties of such a chromoprotein.

DISCLOSURE OF THE INVENTION

It is an object of the present invention to provide a novel fluorescent protein derived from *Montipora* sp., *Acropora* sp., and *Lobophytum crassum*.

It is another object of the present invention to provide a fluorescent protein having a sharper spectrum than the wide excitation spectrum of the conventional RFP (DsRed; CLONTECH).

It is further another object of the present invention to provide a novel chromoprotein derived from *Actinia equina*, which absorbs a light with a specific wavelength.

The present inventors have conducted intensive studies directed towards achieving the aforementioned objects. The inventors have designed preferred primers based on information regarding the amino acid sequences of known fluorescent proteins. Thereafter, using the aforementioned primers, the inventors have succeeded in amplifying genes encoding novel fluorescent proteins obtained from cDNA libraries derived from *Montipora* sp., *Acropora* sp., and *Lobophytum crassum*, and in cloning them. Moreover, the present inventors have analyzed the fluorescence properties and pH sensitivity of the obtained fluorescent proteins derived from *Montipora* sp., *Acropora* sp., and *Lobophytum crassum*. Furthermore, the inventors have designed preferred primers based on information regarding the amino acid sequences of known fluorescent proteins, and thereafter, using the aforementioned primers, the inventors have succeeded in amplifying a gene encoding a novel chromoprotein protein obtained from a cDNA library derived from *Actinia equina* presenting a red color, and in cloning it. Still further, the present inventors have analyzed the light absorption properties and pH sensitivity of the obtained chromoprotein derived from *Actinia equina*. The present invention has been completed based on these findings.

Thus, the present invention provides the following (1) to (35):

(1) A fluorescent protein derived from *Montipora* sp., which has the following properties:
[1] the excitation maximum wavelength is 507 nm;
[2] the fluorescence maximum wavelength is 517 nm n;
[3] the molar absorption coefficient at 507 nm is 104,050;
[4] the quantum yield is 0.29; and
[5] the pH sensitivity of light absorption property is pKa of approximately 5.5.

(2) A fluorescent protein derived from *Acropora* sp., which has the following properties:
[1] the excitation maximum wavelength is 505 nm;
[2] the fluorescence maximum wavelength is 516 nm;
[3] the molar absorption coefficient at 505 nm is 53,600;
[4] the quantum yield is 0.67; and
[5] the pH sensitivity of light absorption property is pKa of approximately 6.4.

(3) A fluorescent protein derived from *Acropora* sp., which has the following properties:
[1] the excitation maximum wavelength is 472 nm;
[2] the fluorescence maximum wavelength is 496 nm;
[3] the molar absorption coefficient at 472 nm is 27,250;
[4] the quantum yield is 0.90; and
[5] the pH sensitivity of light absorption property is pKa of approximately 6.6.

(4) A fluorescent protein derived from *Montipora* sp., which has the following properties:
[1] the excitation maximum wavelength is 557 mm;
[2] the fluorescence maximum wavelength is 574 nm;
[3] the molar absorption coefficient at 557 nm is 41,750;
[4] the quantum yield is 0.41; and
[5] the pH sensitivity of light absorption property is pKa<approximately 4.0.

(5) A chromoprotein derived from *Actinia equina*, which has the following properties:
[1] the absorption maximum wavelength is 592 nm;
[2] the molar absorption coefficient at 592 nm is 87,000; and
[3] the pH sensitivity of light absorption property is stable in the range between pH 5 and 10.

(6) A fluorescent protein derived from *Lobophytum crassum*, which has the following properties:
[1] the excitation maximum wavelength is 482 nm;
[2] the fluorescence maximum wavelength is 498 nm;
[3] the molar absorption coefficient at 482 nm is 71,000;
[4] the quantum yield is 0.41; and
[5] the pH sensitivity of the fluorescence maximum is stable in the range between pH 4 and 10.
(7) A fluorescent protein having either the following amino acid sequence (a) or (b):
(a) an amino acid sequence shown in SEQ ID NO: 1; or
(b) an amino acid sequence, which comprises a deletion, substitution, and/or addition of one or several amino acids with respect to the amino acid sequence shown in SEQ ID NO: 1, and which has a fluorescence.
(8) A fluorescent protein having either the following amino acid sequence (a) or (b):
(a) an amino acid sequence shown in SEQ ID NO: 3; or
(b) an amino acid sequence, which comprises a deletion, substitution, and/or addition of one or several amino acids with respect to the amino acid sequence shown in SEQ ID NO: 3, and which has a fluorescence.
(9) A fluorescent protein having either the following amino acid sequence (a) or (b):
(a) an amino acid sequence shown in SEQ ID NO: 5 or 7; or
(b) an amino acid sequence, which comprises a deletion, substitution, and/or addition of one or several amino acids with respect to the amino acid sequence shown in SEQ ID NO: 5 or 7, and which has a fluorescence.
(10) A fluorescent protein having either the following amino acid sequence (a) or (b):
(a) an amino acid sequence shown in SEQ ID NO: 9; or
(b) an amino acid sequence, which comprises a deletion, substitution, and/or addition of one or several amino acids with respect to the amino acid sequence shown in SEQ ID NO: 9, and which has a fluorescence.
(11) A chromoprotein having either the following amino acid sequence (a) or (b):
(a) an amino acid sequence shown in SEQ ID NO: 11; or
(b) an amino acid sequence, which comprises a deletion, substitution, and/or addition of one or several amino acids with respect to the amino acid sequence shown in SEQ ID NO: 11, and which has light-absorbing properties.
(12) A fluorescent protein having either the following amino acid sequence (a) or (b):
(a) an amino acid sequence shown in SEQ ID NO: 13; or
(b) an amino acid sequence, which comprises a deletion, substitution, and/or addition of one or several amino acids with respect to the amino acid sequence shown in SEQ ID NO: 13, and which has fluorescence.
(13) DNA encoding the protein according to any one of (1) to (12) above.
(14) DNA of either the following (a) or (b):
(a) DNA encoding an amino acid sequence shown in SEQ ID NO: 1; or
(b) DNA which has an amino acid sequence comprising a deletion, substitution, and/or addition of one or several amino acids with respect to the amino acid sequence shown in SEQ ID NO: 1, and which encodes a fluorescent protein.
(15) DNA having either the following nucleotide sequence (a) or (b):
(a) a nucleotide sequence shown in SEQ ID NO: 2; or
(b) a nucleotide sequence which comprises a deletion, substitution, and/or addition of one or several nucleotides with respect to the nucleotide sequence shown in SEQ ID NO: 2, and which encodes a fluorescent protein.
(16) DNA of either the following (a) or (b):
(a) DNA encoding an amino acid sequence shown in SEQ ID NO: 3; or
(b) DNA which has an amino acid sequence comprising a deletion, substitution, and/or addition of one or several amino acids with respect to the amino acid sequence shown in SEQ ID NO: 3, and which encodes a fluorescent protein.
(17) DNA having either the following nucleotide sequence (a) or (b):
(a) a nucleotide sequence shown in SEQ ID NO: 4; or
(b) a nucleotide sequence which comprises a deletion, substitution, and/or addition of one or several nucleotides with respect to the nucleotide sequence shown in SEQ ID NO: 4, and which encodes a fluorescent protein.
(18) DNA of either the following (a) or (b):
(a) DNA encoding an amino acid sequence shown in SEQ ID NO: 5 or 7; or
(b) DNA which has an amino acid sequence comprising a deletion, substitution, and/or addition of one or several amino acids with respect to the amino acid sequence shown in SEQ ID NO: 5 or 7, and which encodes a fluorescent protein.
(19) DNA having either the following nucleotide sequence (a) or (b):
(a) a nucleotide sequence shown in SEQ ID NO: 6 or 8; or
(b) a nucleotide sequence which comprises a deletion, substitution, and/or addition of one or several nucleotides with respect to the nucleotide sequence shown in SEQ ID NO: 6 or 8, and which encodes a fluorescent protein.
(20) DNA of either the following (a) or (b):
(a) DNA encoding an amino acid sequence shown in SEQ ID NO: 9; or
(b) DNA which has an amino acid sequence comprising a deletion, substitution, and/or addition of one or several amino acids with respect to the amino acid sequence shown in SEQ ID NO: 9, and which encodes a fluorescent protein.
(21) DNA having either the following nucleotide sequence (a) or (b):
(a) a nucleotide sequence shown in SEQ ID NO: 10; or
(b) a nucleotide sequence which comprises a deletion, substitution, and/or addition of one or several nucleotides with respect to the nucleotide sequence shown in SEQ ID NO: 10, and which encodes a fluorescent protein.
(22) DNA of either the following (a) or (b):
(a) DNA encoding an amino acid sequence shown in SEQ ID NO: 11; or
(b) DNA which has an amino acid sequence comprising a deletion, substitution, and/or addition of one or several amino acids with respect to the amino acid sequence shown in SEQ ID NO: 11, and which encodes a protein having light-absorbing properties.
(23) DNA having either the following nucleotide sequence (a) or (b):
(a) a nucleotide sequence shown in SEQ ID NO: 12; or
(b) a nucleotide sequence which comprises a deletion, substitution, and/or addition of one or several nucleotides with respect to the nucleotide sequence shown in SEQ ID NO: 12, and which encodes a protein having light-absorbing properties.
(24) DNA of either the following (a) or (b):
(a) DNA encoding an amino acid sequence shown in SEQ ID NO: 13; or
(b) DNA which has an amino acid sequence comprising a deletion, substitution, and/or addition of one or several amino acids with respect to the amino acid sequence shown in SEQ ID NO: 13, and which encodes a fluorescent protein.

(25) DNA having either the following nucleotide sequence (a) or (b):
(a) a nucleotide sequence shown in SEQ ID NO: 14; or
(b) a nucleotide sequence which comprises a deletion, substitution, and/or addition of one or several nucleotides with respect to the nucleotide sequence shown in SEQ ID NO: 14, and which encodes a fluorescent protein.
(26) A recombinant vector having the DNA according to any one of (13) to (25) above.
(27) A transformant having the DNA according to any one of (13) to (25) above or the recombinant vector according to (26) above.
(28) A fusion fluorescent protein, which consists of the fluorescent protein according to any one of (1) to (4), (6), (7) to (10), and (12) above, and another protein.
(29) The fusion fluorescent protein according to (28) above, wherein another protein is a protein that localizes in a cell.
(30) The fusion fluorescent protein according to (28) or (29) above, wherein another protein is a protein specific to a cell organella.
(31) A fusion protein, which consists of the chromoprotein according to (5) or (11) above and another protein.
(32) A method for analyzing the localization or dynamics of a protein in a cell, which is characterized in that the fusion fluorescent protein according to any one of (28) to (30) above is allowed to express in the cell.
(33) A method for analyzing physiologically active substances, which is characterized in that the FRET (fluorescence resonance energy transfer) method is carried out using the chromoprotein according to (5) or (11) above as an acceptor protein.
(34) A fluorescent reagent kit, which comprises: the fluorescent protein of any one of (1) to (4), (6), (7) to (10), and (12) above; the DNA of any one of (14) to (21), (24), and (25) above; the recombinant vector of (26) above; the transformant of (27) above; or the fusion fluorescent protein of any of (28) to (30).
(35) An absorbance reagent kit, which comprises: the chromoprotein of (5) or (11) above; the DNA of (22) or (23) above; the recombinant vector of (26) above; the transformant of (27) above; or the fusion protein of (31) above.

BEST MODE FOR CARRYING OUT THE INVENTION

Figure 1:
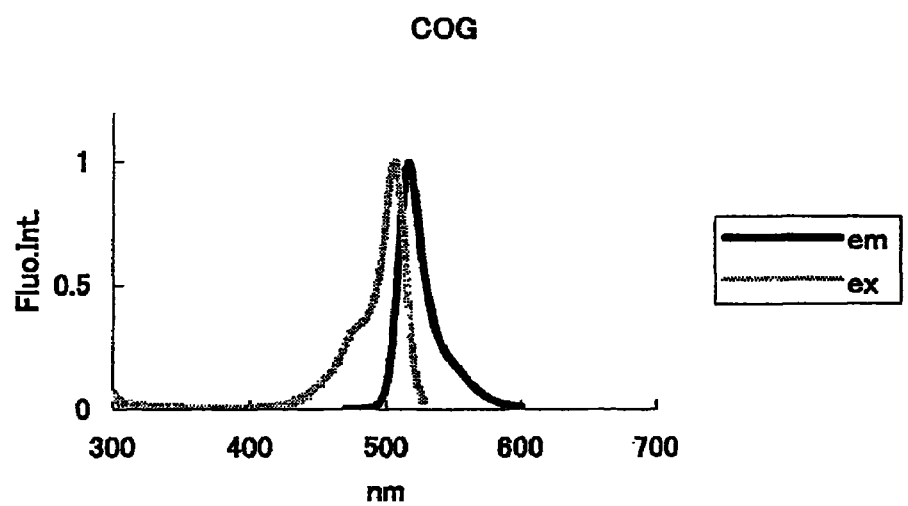
FIG. 1 shows the fluorescence spectrum and excitation spectrum of the fluorescent protein (COG) of the present invention derived from *Montipora* sp. (FIG. A), the absorption spectrum of the fluorescent protein (COG) (FIG. B), and the pH sensitivity of the fluorescent protein (COG) (FIG. C). In FIG. C, the horizontal axis represents pH value, and the longitudinal axis represents absorbance.
Figure 1:
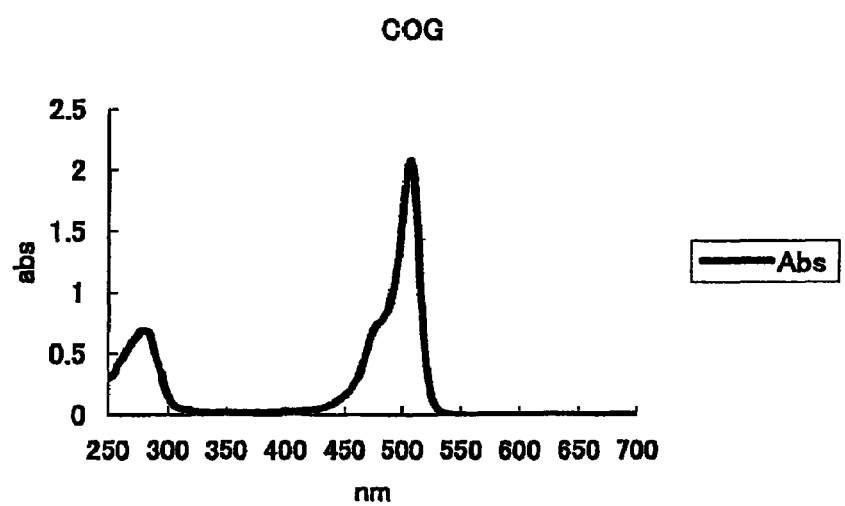
Figure 1:
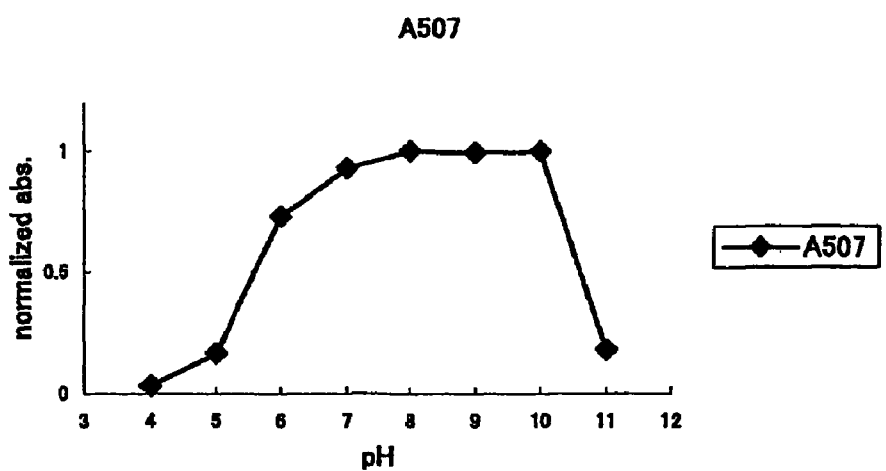

The embodiments of the present invention will be described in detail below.
(1) Fluorescent Proteins and Chromoprotein of the Present Invention
The first fluorescent protein of the present invention is derived from *Montipora* sp., and it has the following properties:
[1] the excitation maximum wavelength is 507 nm;
[2] the fluorescence maximum wavelength is 517 nm;
[3] the molar absorption coefficient at 507 nm is 104,050;
[4] the quantum yield is 0.29; and
[5] the pH sensitivity of light absorption property is pKa of approximately 5.5.
*Montipora* sp. is one kind of coral, which belongs to Cnidaria, Anthozoa, Hexacorallia, Seleractinia, Artrocoeniidae. This coral often forms a massive or covered colony.
As described in examples below, the first fluorescent protein of the present invention has an excitation maximum wavelength of 507 nm and a fluorescence maximum wavelength of 517 nm. In addition, its molar absorption coefficient at 507 nm is 104,050, and its quantum yield is 0.29. The molar absorption coefficient represents the amount of photon absorbed per mole of a fluorescent molecule. The quantum yield is a numerical value representing the degree of the absorbed photon that can be emitted as a fluorescence.
A specific example of the first fluorescent protein of the present invention is a fluorescent protein having either the following amino acid sequence (a) or (b):
(a) an amino acid sequence shown in SEQ ID NO: 1; or
(b) an amino acid sequence, which comprises a deletion, substitution, and/or addition of one or several amino acids with respect to the amino acid sequence shown in SEQ ID NO: 1, and which has a fluorescence.
The second fluorescent protein of the present invention is derived from *Acropora* sp., and it has the following properties:
[1] the excitation maximum wavelength is 505 nm;
[2] the fluorescence maximum wavelength is 516 nm;

[3] the molar absorption coefficient at 505 nm is 53,600;
[4] the quantum yield is 0.67; and
[5] the pH sensitivity of light absorption property is pKa of approximately 6.4.

*Acropora* sp. is one kind of coral, which belongs to Cnidaria, Anthozoa, Hexacorallia, Seleractinia, Artrocoeniidae. This coral often forms a ramiform or tabular colony.

As described in examples below, the second fluorescent protein of the present invention has an excitation maximum wavelength of 505 nm and a fluorescence maximum wavelength of 516 nm. In addition, its molar absorption coefficient at 505 nm is 53,600, and its quantum yield is 0.67. The molar absorption coefficient represents the amount of photon absorbed per mole of a fluorescent molecule. The quantum yield is a numerical value representing the degree of the absorbed photon that can be emitted as a fluorescence.

A specific example of the second fluorescent protein of the present invention is a fluorescent protein having either the following amino acid sequence (a) or (b):
(a) an amino acid sequence shown in SEQ ID NO: 3; or
(b) an amino acid sequence, which comprises a deletion, substitution, and/or addition of one or several amino acids with respect to the amino acid sequence shown in SEQ ID NO: 3, and which has a fluorescence.

The third fluorescent protein of the present invention is derived from *Acropora* sp., and it has the following properties:
[1] the excitation maximum wavelength is 472 nm;
[2] the fluorescence maximum wavelength is 496 nm;
[3] the molar absorption coefficient at 472 nm is 27,250;
[4] the quantum yield is 0.90; and
[5] the pH sensitivity of light absorption property is pKa of approximately 6.6.

As described in examples below, the third fluorescent protein of the present invention has an excitation maximum wavelength of 472 nm and a fluorescence maximum wavelength of 496 nm. In addition, its molar absorption coefficient at 472 nm is 27,250, and its quantum yield is 0.90. The molar absorption coefficient represents the amount of photon absorbed per mole of a fluorescent molecule. The quantum yield is a numerical value representing the degree of the absorbed photon that can be emitted as a fluorescence.

A specific example of the third fluorescent protein of the present invention is a fluorescent protein having either the following amino acid sequence (a) or (b):
(a) the amino acid sequence shown in SEQ ID NO: 5 or 7; or
(b) an amino acid sequence, which comprises a deletion, substitution, and/or addition of one or several amino acids with respect to the amino acid sequence shown in SEQ ID NO: 5 or 7, and which has fluorescence.

The fourth fluorescent protein of the present invention is derived from *Montipora* sp., and it has the following properties:
[1] the excitation maximum wavelength is 557 nm;
[2] the fluorescence maximum wavelength is 574 nm;
[3] the molar absorption coefficient at 557 nm is 41,750;
[4] the quantum yield is 0.41; and
[5] the pH sensitivity of light absorption property is pKa<approximately 4.0.

As described in examples below, the fourth fluorescent protein of the present invention has an excitation maximum wavelength of 557 nm and a fluorescence maximum wavelength of 574 nm. In addition, its molar absorption coefficient at 557 nm is 41,750, and its quantum yield is 0.41. The molar absorption coefficient represents the amount of photon absorbed per mole of a fluorescent molecule. The quantum yield is a numerical value representing the degree of the absorbed photon that can be emitted as a fluorescence.

A specific example of the fourth fluorescent protein of the present invention is a fluorescent protein having either the following amino acid sequence (a) or (b):
(a) the amino acid sequence shown in SEQ ID NO: 9; or
(b) an amino acid sequence, which comprises a deletion, substitution, and/or addition of one or several amino acids with respect to the amino acid sequence shown in SEQ ID NO: 9, and which has a fluorescence.

The chromoprotein of the present invention is derived from *Actinia equina*, and it has the following properties:
[1] the absorption maximum wavelength is 592 nm;
[2] the molar absorption coefficient at 592 nm is 87,000; and
[3] the pH sensitivity of light absorption property is stable in the range between pH 5 and 10.

*Actinia equina* is one kind of sea anemone, which belongs to Cnidaria, Anthozoa, Hexacorallia, Actiniaria, Actimidae. This sea anemone is commonly found in surf zones in Kyushu and more northern areas in Japan. When *Actinia equina* extends its tentacles, it seems to be a red flow that opens in water.

In the examples of the present specification described below, the chromoprotein having the aforementioned properties has been isolated using *Actinia equina* as a starting material. However, there are some cases where the chromoprotein of the present invention can be obtained from sea anemone other than *Actinia equina*. Such chromoproteins are also included in the scope of the present invention.

As described in examples below, the chromoprotein of the present invention has an absorption maximum wavelength of 592 nm and a molar absorption coefficient of 87,000 at 592 nm.

The molar absorption coefficient represents the amount of photon absorbed per mole of a fluorescent molecule. The quantum yield is a numerical value representing the degree of the absorbed photon that can be emitted as a fluorescence. Since the quantum yield of the chromoprotein of the present invention is extremely low, it emits almost no fluorescence. Because of such a property, the chromoprotein of the present invention can be used (1) as an acceptor molecule (energy receptor) in FRET; (2) for the development of a system for converting the energy of a light irradiated to energy other than the light energy; or (3) for introducing a mutation into the amino acid sequence of a protein, so as to modify it such that it emits a fluorescence.

In addition, the chromoprotein of the present invention is characterized in that its pH sensitivity of the light absorption property is stable in the range between pH 5 and 10. That is to say, in the case of the chromoprotein of the present invention, the peak value of its absorption spectrum does not fluctuate so much in the range between pH 5 and 10. Accordingly, the chromoprotein of the present invention can be used in a wide range of pH environment under the same above conditions, and it can be used in living bodies without rigid constraints.

A specific example of the chromoprotein of the present invention is a chromoprotein having either the following amino acid sequence (a) or (b):
(a) an amino acid sequence shown in SEQ ID NO: 11; or
(b) an amino acid sequence, which comprises a deletion, substitution, and/or addition of one or several amino acids with respect to the amino acid sequence shown in SEQ ID NO: 11, and which has light-absorbing properties.

The fifth fluorescent protein of the present invention is derived from *Lobophytum crassum*, and it has the following properties:
[1] the excitation maximum wavelength is 482 nm;
[2] the fluorescence maximum wavelength is 498 nm;
[3] the molar absorption coefficient at 482 nm is 71,000;
[4] the quantum yield is 0.41; and
[5] the pH sensitivity of the fluorescence maximum is stable in the range between pH 4 and 10.

*Lobophytum crassum* is one kind of coral, which belongs to Cnidaria, Anthozoa, Octocorallia.

As described in examples below, the fifth fluorescent protein of the present invention has an excitation maximum wavelength of 482 nm and a fluorescence maximum wavelength of 498 nm. In addition, its molar absorption coefficient at 482 nm is 71,000, and its quantum yield is 0.41. The molar absorption coefficient represents the amount of photon absorbed per mole of a fluorescent molecule. The quantum yield is a numerical value representing the degree of the absorbed photon that can be emitted as a fluorescence.

A specific example of the fifth fluorescent protein of the present invention is a fluorescent protein having either the following amino acid sequence (a) or (b):
(a) an amino acid sequence shown in SEQ ID NO: 13; or
(b) an amino acid sequence, which comprises a deletion, substitution, and/or addition of one or several amino acids with respect to the amino acid sequence shown in SEQ ID NO: 13, and which has a fluorescence.

The scope of "one or several" in the phrase "an amino acid sequence comprising a deletion, substitution and/or addition of one or several amino acids" used herein is not particularly limited. For example, it means 1 to 20, preferably 1 to 10, more preferably 1 to 7, further preferably 1 to 5, and particularly preferably 1 to 3.

The term "has a fluorescence" covers all of the cases where any fluorescence is given. Various properties such as fluorescence intensity, excitation wavelength, fluorescence wavelength or pH sensitivity, may be changed or may remain unchanged, as compared with the case of the protein having an amino acid sequence shown in SEQ ID NO: 1.

The term "light-absorbing properties" is used in the present specification to mean properties capable of absorbing a light with a certain wavelength. For example, as with the chromoprotein described in the present specification, an absorption maximum wavelength may be 592 nm, or the value of such an absorption maximum wavelength may be shifted. The pH sensitivity of the light absorption property is preferably stable in the range between pH 5 and 10.

As stated above, the chromoprotein of the present invention having the amino acid sequence shown in SEQ ID NO: 11 of the sequence listing emits almost no fluorescence. In the present invention, a deletion, substitution, and/or addition of one or several amino acids may be introduced into the amino acid sequence shown in SEQ ID NO: 11, so as to produce a protein emitting a stronger fluorescence. The thus produced protein is also included in the scope of the present invention.

The method of obtaining the fluorescent protein and the chromoproteins of the present invention is not particularly limited. The proteins may be either a protein synthesized by chemosynthesis, or recombinant protein produced by a gene recombination technique.

Where a recombinant protein is produced, it is necessary to obtain DNA encoding the protein. Appropriate primers are designed by using information regarding the amino acid sequence shown in SEQ ID NO: 1, 3, 5, 7, 9, 11 or 13 of the sequence listing of the present specification and the nucleotide sequence shown in SEQ ID NO: 2, 4, 6, 8, 10, 12 or 14 thereof. Using these primers, PCR is carried out by using cDNA library derived from *Montipora* sp., *Acropora* sp., *Actinia equine*, or *Lobophytum crassum* as a template, so that DNA encoding the fluorescent protein or the chromoprotein of the present invention can be obtained. Where a partial fragment of DNA encoding the fluorescent protein or the chromoprotein of the present invention are obtained by the above-described PCR, the produced DNA fragments are ligated to one another by a gene recombination technique, so that DNA encoding the desired fluorescent protein or the chromoprotein can be obtained. The fluorescent protein or the chromoprotein of the present invention can be produced by introducing this DNA into an appropriate expression system. Expression in an expression system will be described later in the present specification.

(2) DNA of the Present Invention

The present invention provides genes encoding the fluorescent proteins or chromoprotein of the present invention.

A specific example of DNA encoding the fluorescent proteins of the present invention is either the following DNA (a) or (b):
(a) DNA encoding an amino acid sequence shown in SEQ ID NO: 1, 3, 5, 7, 9, or 13; or
(b) DNA, which encodes an amino acid sequence comprising a deletion, substitution, and/or addition of one or several amino acids with respect to the amino acid sequence shown in SEQ ID NO: 1, 3, 5, 7, 9, or 13, and which encodes a fluorescent protein.

Another specific example of DNA encoding the florescent proteins of the present invention is either the following DNA (a) or (b):
(a) DNA having the nucleotide sequence shown in SEQ ID NO: 2, 4, 6, 8, 10, or 14; or
(b) DNA, which has a nucleotide sequence comprising a deletion, substitution, and/or addition of one or several nucleotides with respect to the nucleotide sequence shown in SEQ ID NO: 2, 4, 6, 8, 10, or 14, and which encodes a fluorescent protein.

A specific example of DNA encoding the chromoprotein of the present invention is either the following DNA (a) or (b):
(a) DNA encoding an amino acid sequence shown in SEQ ID NO: 11; or
(b) DNA, which has an amino acid sequence comprising a deletion, substitution, and/or addition of one or several amino acids with respect to the amino acid sequence shown in SEQ ID NO: 11, and which encodes a protein having light-absorbing properties.

Another specific example of DNA encoding the chromoprotein of the present invention is DNA having either the following nucleotide sequence (a) or (b):
(a) a nucleotide sequence shown in SEQ ID NO: 12; or
(b) a nucleotide sequence which comprises a deletion, substitution, and/or addition of one or several nucleotides with respect to the nucleotide sequence shown in SEQ ID NO: 12, and which encodes a protein having light-absorbing properties.

The DNA of the present invention can be synthesized by, for example, the phosphoamidite method, or it can also be produced by polymerase chain reaction (PCR) using specific primers. The DNA of the present invention or its fragment is produced by the method described above in the specification.

A method of introducing a desired mutation into a certain nucleic acid sequence is known to a person skilled in the art. For example, known techniques such as a site-directed mutagenesis, PCR using degenerated oligonucleotides, or the exposure of cells containing nucleic acid to mutagens or radioactive rays, are appropriately used, so as to construct DNA having a mutation. Such known techniques are described in, for example, Molecular Cloning: A Laboratory Manual, 2$^{nd}$ Ed., Cold Spring Harbor Laboratory, Cold Spring Harbor, N.Y., 1989; and Current Protocols in Molecular Biology, Supplements 1 to 38, John Wiley & Sons (1987-1997).

(3) Recombinant Vector of the Present Invention

The DNA of the present invention can be inserted into a suitable vector and used. The type of a vector used in the present invention is not particularly limited. For example, it may be either a vector that can autonomously replicate (e.g., a plasmid, etc.), or vector that is incorporated into the genomes of host cells when it is introduced into the host cells and is then replicated together with the chromosome into which it is incorporated.

The vector used in the present invention is preferably an expression vector. In an expression vector, elements necessary for transcription (e.g., a promoter, etc.) are functionally ligated to the DNA of the present invention. The promoter is a DNA sequence which shows a transcriptional activity in host cells, and it is appropriately selected depending on the type of host cells.

Examples of a promoter which can operate in bacterial cells may include a *Bacillus stearothermophilus* maltogenic amylase gene promoter, a *Bacillus licheniformis* alpha-amylase gene promoter, a *Bacillus amyloliquefaciens* BAN amylase gene promoter, a *Bacillus subtilis* alkaline protease gene promoter, a *Bacillus pumilus* xylosidase gene promoter, $P_R$ and $P_L$ promoters of phage rhamda, and lac, trp and tac promoters of *Escherichia coli*.

Examples of a promoter which can operate in mammalian cells may include an SV40 promoter, an MT-1 (metallothionein gene) promoter, and an adenovirus-2 major late promoter. Examples of a promoter which can operate in insect cells may include a polyhedrin promoter, a P10 promoter, an *Autographa californica* polyhedrosis basic protein promoter, a baculovirus immediate-early gene 1 promoter, and a baculovirus 39K delayed-early gene promoter. Examples of a promoter which can be operate in yeast host cells may include promoters derived from yeast glycolytic genes, an alcohol dehydrogenase gene promoter, a TPI1 promoter, and an ADH2-4c promoter.

Examples of a promoter which can operate in filamentous cells may include an ADH3 promoter and a tpiA promoter.

In addition, an appropriate terminator such as a human growth hormone terminator, or a TPI1 terminator or ADH3 terminator for fungal cells, may be functionally bound to the DNA of the present invention, as necessary. The recombinant vector of the present invention may further have elements such as a polyadenylation signal (e.g., one derived from SV40 or the adenovirus 5E1b region), a transcription enhancer sequence (e.g., an SV40 enhancer), or a translation enhancer sequence (e.g., one encoding the adenovirus VA RNA).

The recombinant vector of the present invention may further comprise a DNA sequence which enables the replication of the recombinant vector in host cells. SV40 replication origin is an example of such a sequence (when the host cells are mammalian cells).

The recombinant vector of the present invention may further comprise a selective marker. Examples of such a selective marker may include genes, complements of which are absent from host cells, such as a dihydrofolate reductase (DHFR) gene or a *Shizosaccharomyces pombe* TPI gene, and drug resistant genes such as ampicillin, kanamycin, tetracycline, chloramphenicol, neomycin or hygromycin-resistant genes.

A method for ligating the DNA of the present invention, a promoter and, as desired, a terminator and/or a secretory signal sequence to one another and inserting these items into a suitable vector is known to a person skilled in the art.

(4) Transformant of the Present Invention

A transformant can be produced by introducing the DNA or recombinant vector of the present invention into a suitable host.

Any cell can be used as a host cell into which the DNA or recombinant vector of the present invention is introduced, as long as the DNA construct of the present invention can be expressed therein. Examples of such a cell may include bacteria, yeasts, fungal cells, and higher eukaryotic cells.

Examples of bacteria may include Gram-positive bacteria such as *Bacillus* or *Streptomyces*, and Gram-negative bacteria such as *Escherichia coli*. These bacteria may be transformed by the protoplast method or other known methods, using competent cells.

Examples of mammalian cells may include HEK 293 cells, HeLa cells, COS cells, BHK cells, CHL cells, and CHO cells. A method of transforming mammalian cells and expressing the introduced DNA sequence in the cells is also known. Examples of such a method may include the electroporation, the calcium phosphate method, and the lipofection method.

Examples of yeast cells may include those belonging to Saccharomyces or Shizosaccharomyces. Examples of such cells may include *Saccharomyces cerevisiae* and *Saccharomyces kluyveri*. Examples of a method of introducing a recombinant vector into yeast host cells may include the electroporation, the spheroplast method, and the lithium acetate method.

Examples of other fungal cells may include those belonging to Filamentous fungi such as *Aspergillus, Neurospora, Fusarium* or *Trichoderma*. Where Filamentous fungi are used as host cells, transformation can be carried out by incorporating DNA constructs into host chromosomes, so as to obtain recombinant host cells. Incorporation of DNA constructs into the host chromosomes is carried out by known methods, and such known methods may include homologous recombination and heterologous recombination.

Where insect cells are used as host cells, both a vector into which a recombinant gene is introduced and a baculovirus are co-introduced into insect cells, and a recombinant virus is obtained in the culture supernatant of the insect cells. Thereafter, insect cells are infected with the recombinant virus, so as to allow the cells to express proteins (described in, for example, Baculovirus Expression Vectors, A Laboratory Manual; and Current Protocols in Molecular Biology, Bio/Technology, 6, 47 (1988)).

The *Autographa californica* nuclear polyhedrosis virus, which is a virus infecting to insects belonging to *Barathra brassicae*, can be used as baculovirus.

Examples of insect cells used herein may include Sf9 and Sf21, which are *Spodoptera frugiperda* ovarian cells [Baculovirus Expression. Vectors, A Laboratory Manual, W. H. Freeman & Company, New York, (1992)], and HiFive (manufactured by Invitrogen), which are *Trichoplusia ni* ovarian cells.

Examples of the method of co-introducing both a vector into which a recombinant gene has been introduced and the above baculovirus into insect cells to prepare a recombinant virus may include the calcium phosphate method and the lipofection method.

The above transformant is cultured in an appropriate nutritive medium under conditions enabling the introduced DNA construct to be expressed. In order to isolate and purify the protein of the present invention from the culture product of the transformant, common methods of isolating and purifying proteins may be used.

For example, where the protein of the present invention is expressed in a state dissolved in cells, after completion of the culture, cells are recovered by centrifugal separation, and the recovered cells are suspended in a water type buffer. Thereafter, the cells are disintegrated using an ultrasonic disintegrator or the like, so as to obtain a cell-free extract. A supernatant is obtained by centrifuging the cell-free extract, and then, a purified sample can be obtained from the supernatant by applying, singly or in combination, the following ordinary protein isolation and purification methods: the solvent extraction, the salting-out method using ammonium sulfate or the like, the desalting method, the precipitation method using an organic solvent, the anion exchange chromatography using resins such as diethylaminoethyl (DEAE) sepharose, the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method, and the electrophoresis such as isoelectric focusing.

(5) Use of the Fluorescent Protein of the Present Invention and a Fusion Fluorescent Protein Comprising the Same The fluorescent protein of the present invention can be fused with another protein, so as to construct a fusion fluorescent protein.

A method of obtaining the fusion fluorescent protein of the present invention is not particularly limited. It may be either a protein synthesized by chemosynthesis, or recombinant protein produced by a gene recombination technique.

Where a recombinant protein is produced, it is necessary to obtain DNA encoding the protein. Appropriate primers are designed using the information regarding the amino acid sequence shown in SEQ ID NO: 1, 3, 5, 7, 9 or 13 of the sequence listing of the present specification and the nucleotide sequence shown in SEQ ID NO: 2, 4, 6, 8, 10 or 14 thereof. Using these primers, PCR is carried out using a DNA fragment containing the gene of the fluorescent protein of the present invention as a template, so as to produce DNA fragments necessary for construction of the DNA encoding the fluorescent protein of the present invention. Moreover, DNA fragment encoding a protein to be fused is also obtained in the same above manner.

Subsequently, the thus obtained DNA fragments are ligated to one another by a gene recombination technique, so that DNA encoding the desired fusion fluorescent protein can be obtained. This DNA is then introduced into an appropriate expression system, so that the fusion fluorescent protein of the present invention can be produced.

The fluorescent protein of the present invention has an extremely high utility value as a marker. This is to say, the fluorescent protein of the present invention is purified as a fusion protein with an amino acid sequence to be tested, and the fusion protein is introduced into cells by methods such as the microinjection. By observing the distribution of the fusion protein over time, targeting activity of the amino acid sequence to be tested can be detected in the cells.

The type of another protein (an amino acid sequence to be tested) with which the fluorescent protein of the present invention is fused is not particularly limited. Preferred examples may include proteins localizing in cells, proteins specific for intracellular organelles, and targeting signals (e.g., a nuclear transport signal, a mitochondrial presequence, etc.). In addition, the fluorescent protein of the present invention can be expressed in cells and used, as well as being introduced into cells by the microinjection or the like. In this case, a vector into which the DNA encoding the fluorescent protein of the present invention is inserted in such a way that it can be expressed, is introduced into host cells.

Moreover, the fluorescent protein of the present invention can also be used as a reporter protein to determine promoter activity. This is to say, a vector is constructed such that DNA encoding the fluorescent protein of the present invention is located downstream of a promoter to be tested, and the vector is then introduced into host cells. By detecting the fluorescence of the fluorescent protein of the present invention which is emitted from the cells, the activity of the promoter to be tested can be determined. The type of a promoter to be tested is not particularly limited, as long as it operates in host cells.

A vector used to detect the targeting activity of the above amino acid sequence to be tested or to determine promoter activity is not particularly limited. Examples of a vector preferably used for animal cells may include pNEO (P. Southern, and P. Berg (1982) J. Mol. Appl. Genet. 1: 327), pCAGGS (H. Niwa, K. Yamamura, and J. Miyazaki, Gene 108, 193-200 (1991)), pRc/CMV (manufactured by Invitrogen), and pCDM8 (manufactured by Invitrogen). Examples of a vector preferably used for yeasts may include pRS303, pRS304, pRS305, pRS306, pRS313, pRS314, pRS315, pRS316 (R. S. Sikorski and P. Hieter (1989) Genetics 122: 19-27), pRS423, pRS424, pRS425, pRS426 (T. W. Christianson, R. S. Sikorski, M. Dante, J. H. Shero, and P. Hieter (1992) Gene 110: 119-122).

In addition, the type of cells used herein is also not particularly limited. Various types of animal cells such as L cells, BalbC-3T3 cells, NIH3T3 cells, CHO (Chinese hamster ovary) cells, HeLa cells or NRK (normal rat kidney) cells, yeast cells such as *Saccharomyces cerevisiae*, *Escherichia coli* cells, or the like can be used. Vector can be introduced into host cells by common methods such as the calcium phosphate method or the electroporation.

The above obtained fusion fluorescent protein of the present invention wherein the fluorescent protein of the present invention is fused with another protein (referred to as a protein X) is allowed to be expressed in cells. By monitoring a fluorescence emitted, it becomes possible to analyze the localization or dynamics of the protein X in cells. That is, cells transformed or transfected with DNA encoding the fusion fluorescent protein of the present invention are observed with a fluorescence microscope, so that the localization and dynamics of the protein X in the cells can be visualized and thus analyzed.

For example, by using a protein specific for an intracellular organella as a protein X, the distribution and movement of a nucleus, a mitochondria, an endoplasmic reticulum, a Golgi body, a secretory vesicle, a peroxisome, etc., can be observed.

Moreover, for example, axis cylinders or dendrites of the nerve cells show an extremely complicated change in strikes in an individual who is under development. Accordingly, fluorescent labeling of these sites enables a dynamic analysis.

The fluorescence of the fluorescent protein of the present invention can be detected with a viable cell. Such detection can be carried out using, for example, a fluorescence microscope (Axiophoto Filter Set 09 manufactured by Carl Zeiss) or an image analyzer (Digital Image Analyzer manufactured by ATTO).

The type of a microscope can be appropriately selected depending on purposes. Where frequent observation such as pursuit of a change over time is carried out, an ordinary incident-light fluorescence microscope is preferable. Where observation is carried out while resolution is emphasized, for example, in the case of searching localization in cells specifically, a confocal laser scanning microscope is preferable. In terms of maintenance of the physiological state of cells and prevention from contamination, an inverted microscope is preferable as a microscope system. When an erecting microscope with a high-powered lens is used, a water immersion lens can be used.

A filter set can be appropriately selected depending on the fluorescence wavelength of a fluorescent protein. In the case of the first and second fluorescent proteins of the present invention, a filter having an excitation light between approximately 490 and 510 nm and a fluorescence between approximately 510 and 530 nm is preferably used. In the case of the third fluorescent proteins of the present invention, a filter having an excitation light between approximately 460 and 480 nm and a fluorescence between approximately 480 and 510 nm is preferably used. In the case of the fourth fluorescent protein of the present invention, a filter having an excitation light between approximately 550 and 565 nm and a fluorescence between approximately 570 and 580 nm is preferably used. In the case of the fifth fluorescent protein of the present invention, a filter having an excitation light between approximately 470 and 490 nm and a fluorescence between approximately 490 and 510 nm is preferably used.

When viable cells are observed over time using a fluorescence microscope, a high sensitive cooled CCD camera is used, since photography is carried out in a short time. In the case of the cooled CCD camera, CCD is cooled to decrease thermal noise, so that a weak fluorescence image can be clearly photographed by exposure in a short time.

(6) Use of the Chromoprotein of the Present Invention and a Fusion Protein Comprising the Same The chromoprotein of the present invention can be fused with another protein, so as to construct a fusion protein. The type of said another protein to be fused to the chromoprotein of the present invention is not particularly limited, and preferred examples may include a protein which interacts with another molecule. The examples may include a receptor protein or ligand thereof, antigen, antibody and the like.

A method of obtaining the fusion protein of the present invention is not particularly limited. It may be either a protein synthesized by chemosynthesis, or recombinant protein produced by a gene recombination technique.

Where a recombinant fusion protein is produced, it is necessary to obtain DNA encoding the protein. The DNA encoding the chromoprotein of the present invention and the DNA encoding the another protein to be fused to the chromoprotein, can be obtained by the method as mentioned above in this specification or by the method similar to it. Then, these DNA fragments are ligated to one another by a gene recombination technique, so that DNA encoding the desired fusion protein can be obtained. This DNA is then introduced into an appropriate expression system, so that the fusion protein of the present invention can be produced.

FRET (fluorescence resonance energy transfer) has been known as a means for analyzing the interaction between molecules. In FRET, for example, a first molecule labeled with a cyan fluorescent protein (CFP) acting as a first fluorescent protein is allowed to coexist with a second molecule labeled with a yellow fluorescent protein (YFP) acting as a second fluorescent protein, so as to allow the yellow fluorescent protein (YFP) to act as an acceptor molecule and to allow the cyan fluorescent protein (CFP) to act as a donor molecule. Thus, FRET (fluorescence resonance energy transfer) is allowed to take place between both molecules, so as to visualize the interaction between the first and second molecules. Namely, in FRET, different dyes are introduced into two types of molecules. One dyes with a higher energy level (a donor molecule) is selectively excited, and the fluorescence of the dye is measured. Long-wavelength fluorescence from the other dye (an acceptor molecule) is also measured. The interaction between the molecules is visualized by using the difference between the amounts of both fluorescences. Only when both dyes are adjacent to each other due to the interaction of the two types of molecules, a decrease in the fluorescence of the donor molecule and an increase in the fluorescence of the acceptor molecule are observed by single wavelength excitation dual wavelength photometry. However, in a case where a chromoprotein is used as an acceptor molecule, a decrease in the fluorescence of the donor molecule occurs only when both dyes are adjacent to each other by the interaction of the two types of molecules. Such a decrease can be observed by single wavelength excitation single wavelength photometry. Thus, the use of the chromoprotein of the present invention enables facilitation of measurement apparatuses.

The chromoprotein of the present invention is particularly advantageous when it is used as an acceptor molecule in FRET (fluorescence resonance energy transfer). That is to say, a fused form (a first fused form) of the chromoprotein of the present invention and a test substance is first produced. Then, a fused form (a second fused form) of another test substance interacting with the above test substance and another fluorescent protein is produced. Thereafter, the first fused form is allowed to interact with the second fused form, and the generated fluorescence is analyzed, so that the interaction between the aforementioned two types of test substances can be analyzed. FRET (fluorescence resonance energy transfer) using the chromoprotein of the present invention may be carried out either in a test tube or in a cell.

(7) Kit of the Present Invention

The present invention provides a kit for analyzing the localization of intracellular components and/or analyzing physiologically active substances, which is characterized in that it comprises at least one selected from the fluorescent protein, the fusion fluorescent protein, the DNA, the recombinant vector, or the transformant, which are described in the present specification. The kit of the present invention can be produced from commonly used materials that are known per se, by using common methods.

Further, the present invention provides a light-absorbing reagent kit, which is characterized in that it comprises at least one selected from the chromoprotein, fusion protein, DNA, recombinant vector or transformant, which are described in the present specification. The kit of the present invention can be produced from commonly used materials that are known per se, by using common methods.

Reagents such as thefluorescent protein, the chromoprotein or the DNA are dissolved in an appropriate solvent, so that the reagents can be prepared in a form suitable for conservation. Water, ethanol, various types of buffer solution, etc. can be used as such a solvent.

The present invention will be further described in the following examples. However, the present invention is not limited by these examples.

EXAMPLES

Example 1

Isolation of Novel Fluorescent Protein Gene (COG) from Stony Coral, and Analysis of Fluorescence Properties Thereof (1) Extraction of Total RNA A fluorescent protein gene was isolated from coral. *Montipora* sp. was used as a material. A frozen *Montipora* sp. was crushed in a mortar, and 7.5 ml of TRIZOL (reagent for RNA preparation/isolation) (GIBCO BRL) was then added to 2 g (wet weight) of the crushed *Montipora* sp. Thereafter, the obtained mixture was homogenized and then centrifuged at 1,500×g for 10 minutes. Thereafter, 1.5 ml of chloroform was added to the obtained supernatant, and the mixture was then stirred for 15 seconds. Thereafter, the mixture was left at rest for 3 minutes. The resultant was then centrifuged at 7,500×g for 15 minutes. Thereafter, 3.75 ml of isopropanol was added to the obtained supernatant, and the mixture was then stirred for 15 seconds, followed by leaving the mixture at rest for 10 minutes. Thereafter, the resultant was centrifuged at 17,000×g for 10 minutes. The obtained supernatant was discarded, and 6 ml of 70% ethanol was added to the residue, followed by centrifugation at 17,000×g for 10 minutes. The obtained supernatant was discarded, and the precipitate was then dissolved in 200 µl of DEPC water. Total RNA dissolved in the DEPC water was 100 times diluted, and the values of O.D.260 and O.D.280 were then measured, so as to determine RNA concentration. As a result, 22 µg of total RNA was obtained.

(2) Synthesis of First Strand cDNA cDNA (33 µl) was synthesized from 4 µg of the total RNA, using a kit for synthesizing first strand cDNA "Ready To Go" (Amersham Pharmacia).

(3) Degenerated PCR

3 µl of the synthesized first strand cDNA (33 µl) was used as a template to carry out PCR.

Primers were produced by making comparison among the amino acid sequences of known fluorescent proteins, extracting similar portions, and converting them to nucleotide sequences.

Primers used:

```
                                            (SEQ ID NO: 15)
5'-GAAGGRTGYGTCAAYGGRCAY-3' (primer 1)

(SEQ ID NO: 16)
5'-ACVGGDCCATYDGVAAGAAARTT-3' (primer 2)
```

I represents inosine; R represents A or G; Y represents C or T; V represents A, C, or G; D represents A, G, or T; S represents C or G; H represents A, T, or C Composition of PCR reaction solution:

| | |
|---|---|
| Template (first strand cDNA) | 3 µl |
| X10 TAQ (polymerase) buffer | 5 µl |
| 2.5 mM dNTPs | 4 µl |
| 100 µM primer 1 | 1 µl |
| 100 µM primer 2 | 1 µl |
| MILLI-Q (reagent grade water) | 35 µl |
| TAQ polymerase (5 U/µl) | 1 µl |

PCR reaction conditions:
94° C. ×1 min (PAD)
94° C. ×30 sec (denaturation)
52° C. ×30 sec (annealing of primers to template)
72° C. ×1 min (primer elongation)

A cycle consisting of the aforementioned 3 steps was repeated 35 times.
72° C.×7 min (final elongation)
4° C. (maintenance)

Using 1 µl of the amplified product obtained in the first PCR reaction as a template, PCR was carried out again under the same above conditions. A 350-bp fragment was cut out via agarose gel electrophoresis, and it was then purified.

(4) Subcloning and Sequencing

The purified DNA fragment was ligated to a pT7-blue vector (Novagen). *Escherichia coli* (TG1) was transformed therewith, and it was then subjected to blue white selection. Plasmid DNA was purified from white colonies of *Escherichia coli*, and the nucleotide sequence of the inserted DNA fragment was determined using a DNA sequencer. Thereafter, the obtained nucleotide sequence was compared with the nucleotide sequences of other fluorescent protein genes, so as to determine whether the nucleotide sequence of the DNA fragment was derived from a fluorescent protein. With regard to those that were determined to be a part of the fluorescent protein genes, the full-length genes were cloned by the 5'-RACE method and the 3'-RACE method.

(5) 5'-RACE Method

In order to determine the nucleotide sequence on the 5'-side of the DNA fragment obtained by the degenerated PCR, the 5'-RACE method was applied using 5'-RACE System for Rapid Amplification of cDNA Ends, Version 2.0 (GIBCO BRL). 5 µg of the total RNA prepared in (1) above was used as a template.

The following primers were used in the first amplification of dC-tailed cDNA:

```
                                            (SEQ ID NO: 17)
5'-GGCCACGCGTCGACTAGTACGGGIIGGGIIGGGIIG-3'
(primer 3);
and (SEQ ID NO: 18)
5'-CCATCTTCAAAGAGAAAAGACCTTT-3' (primer 4)
```

Herein, I represents inosine.

The following primers were used in the second amplification:

```
                                            (SEQ ID NO: 19)
5'-GGCCACGCGTCGACTAGTAC-3' (primer 5);
and (SEQ ID NO: 20)
5'-CATGAGTTCTTGAAATAGTCAAC-3' (primer 6).
```

PCR reaction conditions were applied in accordance with protocols attached to the kit.

The amplified 350-bp band was cut out of the gel via agarose gel electrophoresis and then purified. The purified DNA fragment was ligated to a pT7-blue vector (Novagen). *Escherichia coli* (TG1) was transformed therewith, and it was then subjected to blue white selection. Plasmid DNA was purified from white colonies of *Escherichia coli*, and the nucleotide sequence of the inserted DNA fragment was determined using a DNA sequencer.

(6) 3'-RACE method

The nucleotide sequence on the 3'-side of the DNA fragment obtained by the degenerated PCR was obtained by PCR using a primer prepared based on the information obtained by determination of the nucleotide sequence in (4) above and an oligo dT primer. 3 µl of the first strand cDNA prepared in (2) above was used as a template. The prepared primer was 5'-ATGGCTCTTTCAAAGCGAGGTG-3' (primer 7) (SEQ ID NO: 21).

Composition of PCR reaction solution:

| | |
|---|---|
| Template (first strand cDNA) | 3 µl |
| X10 TAQ (polymerase) buffer | 5 µl |
| 2.5 mM dNTPs | 4 µl |
| 20 µM primer 7 | 1 µl |
| 10 µM oligo dT primer | 1 µl |

-continued

| MILLI-Q (reagent grade water) | 35 µl |
| TAQ polymerase (5 U/µl) | 1 µl |

PCR reaction conditions:
94° C. ×1 minute (PAD)
94° C. ×30 seconds (denaturation)
52° C. ×30 seconds (annealing of primers to template)
72° C. ×1 minute (primer elongation)
4° C. (maintenance)

The amplified band with a length of approximately 1,000 bp was cut out of the gel via agarose gel electrophoresis and then purified. The purified DNA fragment was ligated to a pT7-blue vector (Novagen). *Escherichia coli* (TG1) was transformed therewith, and it was then subjected to blue white selection. Plasmid DNA was purified from white colonies of *Escherichia coli*, and the nucleotide sequence of the inserted DNA fragment was determined using a DNA sequencer.

The obtained full-length nucleotide sequence is shown in SEQ ID NO: 2 of the sequence listing, and the obtained full-length amino acid sequence is shown in SEQ ID NO: 1 thereof. This clone was named COG.

(7) Expression of Protein in *Escherichia coli*

Based on the obtained full-length nucleotide sequence, a primer was produced with a portion corresponding to the N-terminus of the protein. An oligo dT primer was used as a primer corresponding to the C-terminal side thereof. Thereafter, using such primers, PCR was carried out employing the first strand cDNA prepared in (2) above as a template.
Primer used:

```
                                            (SEQ ID NO: 22)
5'-GGGGGATCCGACCATGGCTCTTTCAAAGCGAGGTG-3'
(primer 8)
```

Composition of PCR reaction solution:

| Template (first strand cDNA) | 3 µl |
| X10 PYROBEST (polymerase) buffer | 5 µl |
| 2.5 mM dNTPs | 4 µl |
| 100 µM primer 8 | 1 µl |
| 100 µM oligo dT primer | 1 µl |
| MILLI-Q (reagent grade water) | 35 µl |
| PYROBEST polymerase (5 U/µl) | 1 µl |

PCR reaction conditions:
94° C. ×1 minute (PAD)
94° C. ×30 seconds (denaturation)
52° C. ×30 seconds (annealing of primers to template)
72° C. ×1 minute (primer elongation)
4° C. (maintenance)

The amplified band with a length of approximately 1,000 bp was cut out of the gel via agarose gel electrophoresis and then purified. The purified DNA fragment was subcloned into the BamHI-EcoRI site of a pRSET vector (Invitrogen), and it was then allowed to express in *Escherichia coli* (JM10.9-DE3). The expressed protein was constructed such that His-tag was attached to the N-terminus thereof, and thus it was purified with Ni-Agarose gel (QIAGEN). Purification was carried out in accordance with the attached protocols. Subsequently, the properties of the purified protein were analyzed.

(8) Analysis of Fluorescence Properties

Using a solution comprising 20 µM fluorescent protein (COG), 150 mM KCl, and 50 mM HEPES (pH 7.5), the absorption spectrum of the protein was measured (FIG. 1B). Thereafter, the molar absorption coefficient of the protein was calculated from the value of the peak (507 nm) of the spectrum. The fluorescent protein was diluted with the above buffer solution such that the absorption at 450 nm became 0.002. Its fluorescence spectrum by exciting at 450 nm and its excitation spectrum by a fluorescence at 550 nm were measured (FIG. 1A). Likewise, EGFP (CLONTECH) was diluted such that the absorption at 450 nm became 0.002, and its fluorescence spectrum was measured. Setting the quantum yield of EGFP to 0.6, the quantum yield of the cloned fluorescent protein was obtained. The results are shown in Table 1.

TABLE 1

| | Excitation maximum | Fluorescence maximum | Molar absorption coefficient | Quantum yield | pH sensitivity | Number of amino acids |
|---|---|---|---|---|---|---|
| COG | 507 nm | 517 nm | 104,050 (507 nm) | 0.29 | pKa = 5.5 | 227 |

(9) Measurement of pH Sensitivity

Figure 2:
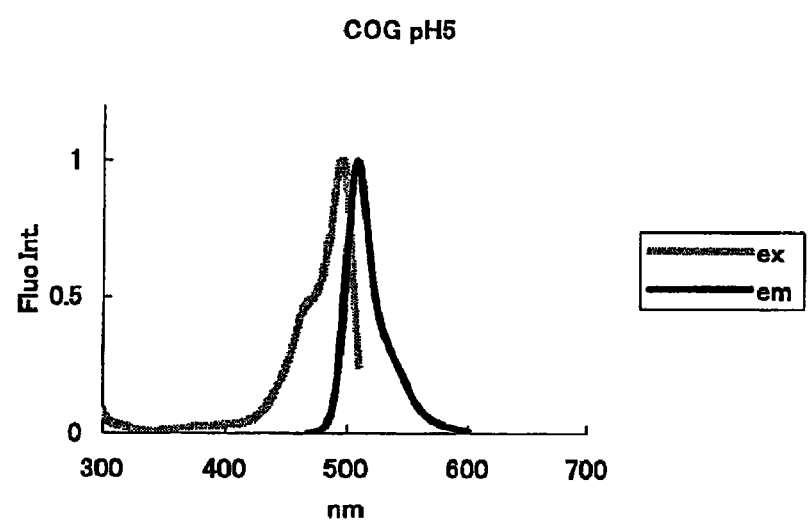
FIG. 2 shows the fluorescence spectrum and excitation spectrum at pH 5 of the fluorescent protein (COG) of the present invention derived from *Montipora* sp. (FIG. A), and the absorption spectrum thereof at pH 5 (FIG. B).
Figure 2:
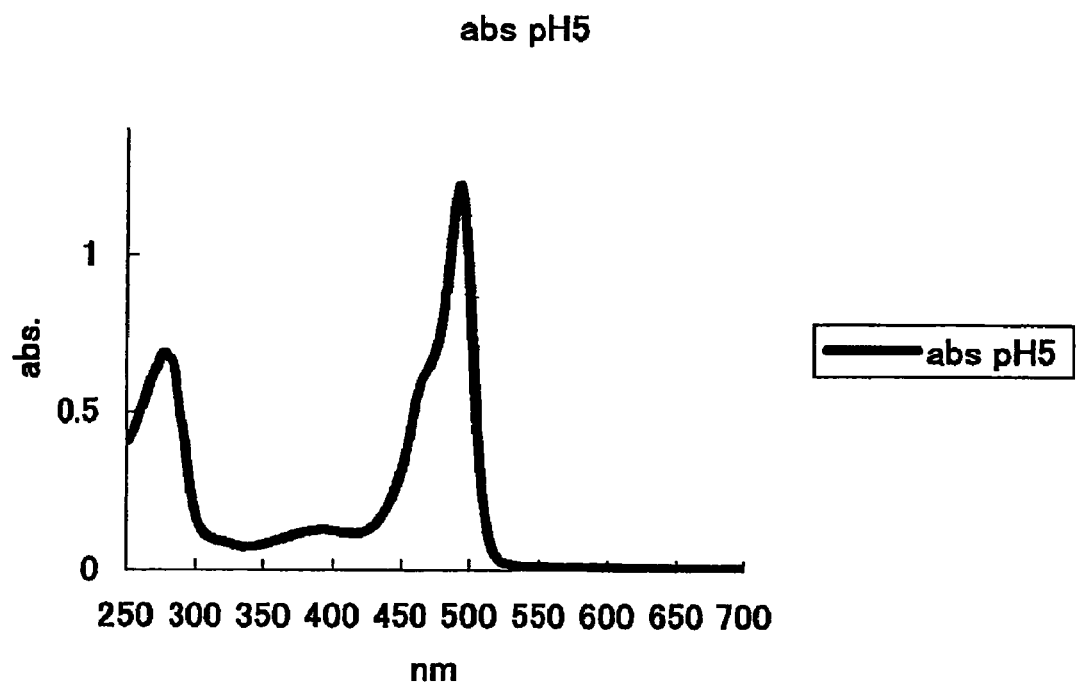

The fluorescent protein was diluted with each of the following buffer solutions to the same concentration. The value of the absorption at 570 nm was determined, and thus the pH sensitivity thereof was measured (FIG. C1). The pH levels of the buffer solutions are as follows.
pH 4 and 5: Acetate buffer
pH 6 and 11: Phosphate buffer
pH 7 and 8: HEPES buffer
pH 9 and 10: Glycine buffer This fluorescent protein has such characteristics that when pH 5 is compared with pH 6 to 10, the absorption peak is shifted to a short wavelength side (from 507 nm to 493 nm), and the fluorescence peak is also shifted to a short wavelength side (from 517 nm to 508 nm). The measurement results are shown in FIGS. 2A and 2B.

Example 2

Isolation of Novel Fluorescent Protein Gene (MIG) from Coral (1) Extraction of Total RNA A fluorescent protein gene was isolated from coral emitting a fluorescence. *Acropora* sp. was used as a material. *Acropora* sp. was crushed with a hammer, and 15 ml of TRIZOL (reagent for RNA preparation/isolation) (GIBCO BRL) was then added to 5 g of the crushed *Montipora* sp. Thereafter, the obtained mixture was stirred and then centrifuged at 1,500×g for 10 minutes. Thereafter, 3 ml of chloroform was added to the obtained supernatant, and the mixture was then stirred for 15 seconds. Thereafter, the mixture was left at rest for 3 minutes. The resultant was then centrifuged at 7,500×g for 15 minutes. Thereafter, 7.5 ml of isopropanol was added to the obtained supernatant, and the mixture was then stirred for 15 seconds, followed by leaving the mixure at rest for 10 minutes. Thereafter, the resultant was centrifuged at 17,000×g for 10 minutes. The obtained supernatant was discarded, and 6 ml of 70% ethanol was added to the residue, followed by centrifugation at 17,000×g for 10 minutes. The obtained supernatant was discarded, and the precipitate was then dissolved in 200 µl of DEPC water. Total RNA dissolved in the DEPC water was 100 times diluted, and the values of O.D.260 and O.D.280 were then measured, so as to determine RNA concentration. As a result, 220 µg of total RNA was obtained.

(2) Synthesis of First Strand cDNA cDNA (33 μl) was synthesized from 5 μg of the total RNA, using a kit for synthesizing first strand cDNA "Ready To Go" (Amersham Pharmacia).

(3) Degenerated PCR

3 μi of the synthesized first strand cDNA (33 μl) was used as a template to carry out PCR. Primers were produced by making comparison among the amino acid sequences of known fluorescent proteins, extracting similar portions, and converting them to nucleotide sequences.

Primers used:

```
                                             (SEQ ID NO: 15)
    5'-GAAGGRTGYGTCAAYGGRCAY-3' (primer 1)

(SEQ ID NO: 16)
    5'-ACVGGDCCATYDGVAAGAAARTT-3' (primer 2)
```

R represents A or G; Y represents C or T; V represents A, C, or G; D represents A, G, or T Composition of PCR reaction solution:

| Template (first strand cDNA) | 3 μl |
|---|---|
| X10 TAQ (polymerase) buffer | 5 μl |
| 2.5 mM dNTPs | 4 μl |
| 100 μM primer 1 | 1 μl |
| 100 μM primer 2 | 1 μl |
| MILLI-Q (reagent grade water) | 35 μl |
| TAQ polymerase (5 U/μl) | 1 μl |

PCR reaction conditions:
94° C. ×1 min (PAD)
94° C. ×30 sec (denaturation)
52° C. ×30 sec (annealing of primers to template)
72° C. ×1 min (primer elongation)

A cycle consisting of the aforementioned 3 steps was repeated 30 times. The annealing temperature was decreased by 0.3° C. for every cycle. The annealing temperature was 43° C. at the time of the 30$^{th}$ cycle.

72° C.×7 min (final elongation)
4° C. (maintenance)

Using 1 μl of the amplified product obtained in the first PCR reaction as a template, PCR was carried out again under the same above conditions. A band with an estimated size of 350 bp was cut out via agarose gel electrophoresis, and it was then purified.

(4) Subcloning and Sequencing

The purified DNA fragment was ligated to a pT7-blue vector (Novagen). Escherichia coli (TG1) was transformed therewith, and it was then subjected to blue white selection. Plasmid DNA was purified from white colonies of Escherichia coli, and the nucleotide sequence of the inserted DNA fragment was determined using a DNA sequencer. Thereafter, the obtained nucleotide sequence was compared with the nucleotide sequences of other fluorescent protein genes, so as to determine whether the nucleotide sequence of the DNA fragment was derived from a fluorescent protein. With regard to those that were determined to be a part of the fluorescent protein genes, the full-length genes were cloned by the 5'-RACE method and the 3'-RACE method.

(5) 5'-RACE Method

In order to determine the nucleotide sequence on the 5'-side of the DNA fragment obtained by the degenerated PCR, the 5'-RACE method was applied using 5'-RAC System for Rapid Amplification of cDNA Ends, Version 2.0 (GIBCO BRL). 3 μg of the total RNA prepared in (1) above was used as a template. The following primers were used in the first amplification of dC-tailed cDNA:

```
                                                (SEQ ID NO: 17)
5'-GGCCACGCGTCGACTAGTACGGGIIGGGIIGGGIIG-3'
(primer 3);
and (SEQ ID NO: 23)
5'- TAGAAATGACCTTTCATATGACATTC -3' (primer 4).
```

Herein, I represents inosine.

The following primers were used in the second amplification:

```
                                                (SEQ ID NO: 19)
    5'-GGCCACGCGTCGACTAGTAC-3' (primer 5);
and (SEQ ID NO: 24)
    5'-TCTGTTTCCATATTGAAAGGCTG-3' (primer 6).
```

PCR reaction conditions were applied in accordance with protocols attached to the kit.

The amplified 500-bp band was cut out of the gel via agarose gel electrophoresis and then purified. The purified DNA fragment was ligated to a pT7-blue vector (Novagen). Escherichia coli (TG1) was transformed therewith, and it was then subjected to blue white selection. Plasmid DNA was purified from white colonies of Escherichia coli, and the nucleotide sequence of the inserted DNA fragment was determined using a DNA sequencer.

(6) 3'-RACE Method

The nucleotide sequence on the 3'-side of the DNA fragment obtained by the degenerated PCR was obtained by PCR, using a primer prepared based on the information obtained by determination of the nucleotide sequence in (4) above and an oligo dT primer. 3 μl of the first strand cDNA prepared in (2) above was used as a template. The prepared primer was

```
                                                (SEQ ID NO: 25)
5'-ATGGTGTCTTATTCAAAGCAAGGCATCGCACA-3' (primer 7).
```

Composition of PCR reaction solution:

| Template (first strand cDNA) | 3 μl |
|---|---|
| X10 TAQ (polymerase) buffer | 5 μl |
| 2.5 mM dNTPs | 4 μl |
| 20 μM primer 7 | 1 μl |
| 10 μM oligo dT primer | 1 μl |
| MILLI-Q (reagent grade water) | 35 μl |
| TAQ polymerase (5 U/μl) | 1 μl |

PCR reaction conditions:
94° C. ×1 minute (PAD)
94° C. ×30 seconds (denaturation)
55° C. ×30 seconds (annealing of primers to template)
72° C. ×1 minute (primer elongation)
4° C. (maintenance)

The amplified band with a length of 900 bp was cut out of the gel via agarose gel electrophoresis and then purified. The purified DNA fragment was ligated to a pT7-blue vector (Novagen). Escherichia coli (TG1) was transformed therewith, and it was then subjected to blue white selection. Plasmid DNA was purified from white colonies of Escherichia coli, and the nucleotide sequence of the inserted DNA fragment was determined using a DNA sequencer.

The obtained full-length nucleotide sequence is shown in SEQ ID NO: 4 of the sequence listing, and the obtained full-length amino acid sequence is shown in SEQ ID NO: 3 thereof. This clone was named MIG.

(7) Expression of Protein in *Escherichia coli*

Using a primer produced with a portion corresponding to the N-terminus of the obtained full-length nucleotide sequence of the protein and an oligo dT primer, PCR was carried out employing the first strand cDNA prepared in (2) above as a template. Primer used:

```
                                                 (SEQ ID NO: 26)
5'-CGGGATCCGACCATGGTGTCTTATTCAAAGCAAGGCATCGCACA-3'
(primer 8)
```

Composition of PCR reaction solution:

| | |
|---|---|
| Template (first strand cDNA) | 3 μl |
| X10 PYROBEST (polymerase) buffer | 5 μl |
| 2.5 mM dNTPs | 4 μl |
| 20 μM primer 8 | 1 μl |
| 20 μM oligo dT primer | 1 μl |
| MILLI-Q (reagent grade water) | 35 μl |
| PYROBEST polymerase (5 U/μl) | 1 μl |

PCR reaction conditions:
94° C. ×1 minute (PAD)
94° C. ×30 seconds (denaturation)
55° C. ×30 seconds (annealing of primers to template)
72° C. ×1 minute (primer elongation)
4° C. (maintenance)

The amplified band with a length of 900 bp was cut out of the gel via agarose gel electrophoresis and then purified. The purified DNA fragment was subcloned into the BamHI-EcoRI site of a pRSET vector (Invitrogen), and it was then allowed to express in *Escherichia coli* (JM109-DE3). The expressed protein was constructed such that His-tag was attached to the N-terminus thereof, and thus it was purified with Ni-Agarose gel (QIAGEN). Purification was carried out in accordance with the attached protocols. Subsequently, the properties of the purified protein were analyzed.

(8) Analysis of Fluorescence Properties

Figure 3:
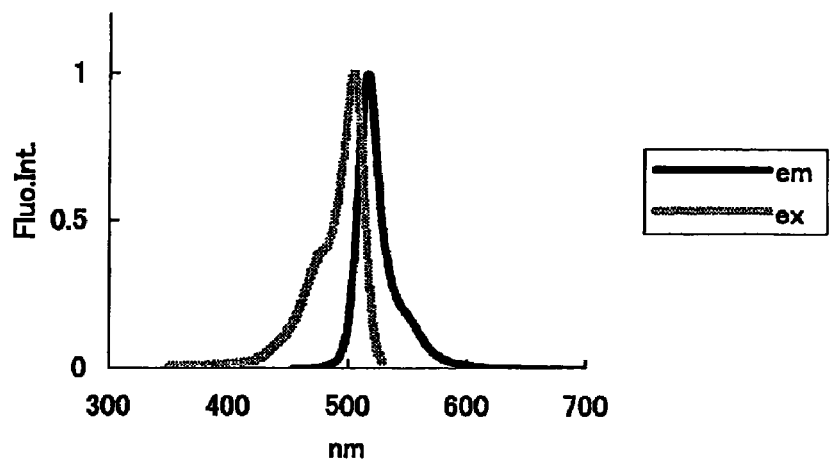
FIG. 3 shows the fluorescence spectrum and excitation spectrum of the fluorescent protein (MIG) of the present invention derived from *Acropora* sp. (FIG. A), the absorption spectrum of the fluorescent protein (MIG) (FIG. B), and the pH sensitivity of the fluorescent protein (MIG) (FIG. C). In FIG. C, the horizontal axis represents pH value, and the longitudinal axis represents absorbance.
Figure 3:
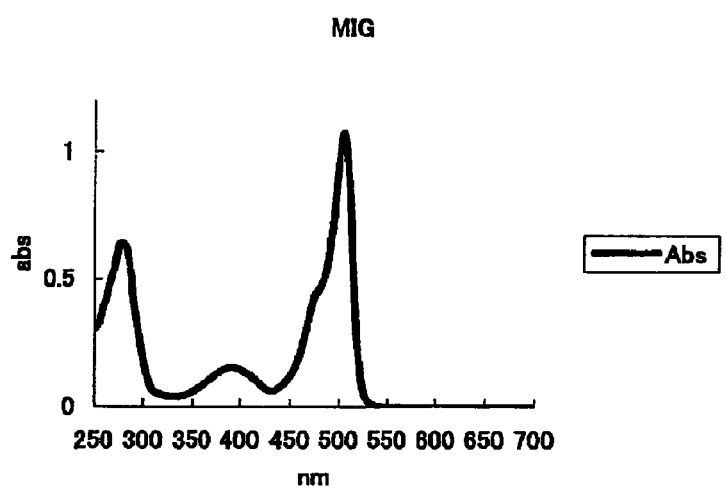
Figure 3:
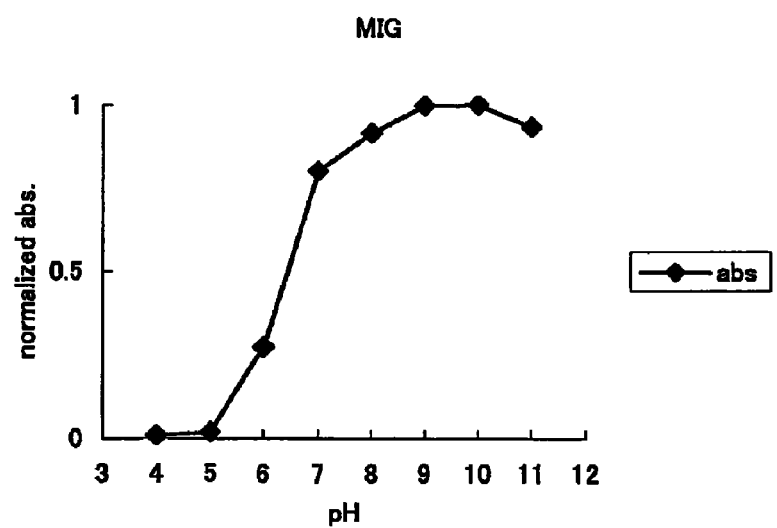

Using a solution comprising 20 μM fluorescent protein (MIG), 50 mM KCl, and 50 mM HEPES (pH 7.4), the absorption spectrum of the protein was measured (FIG. 3B). Thereafter, the molar absorption coefficient of the protein was calculated from the value of the peak (505 nm) of the spectrum. The fluorescent protein was diluted with the above buffer solution such that the absorption at 440 nm became 0.001. Its fluorescence spectrum by exciting at 440 nm and its excitation spectrum by a fluorescence at 540 nm were measured (FIG. 3A). Likewise, EGFP (CLONTECH) was diluted such that the absorption at 440 nm became 0.001, and its fluorescence spectrum was measured. Setting the quantum yield of EGFP to 0.6, the quantum yield of the cloned fluorescent protein was obtained. The measurement results are shown in Table 2.

TABLE 2

| | Excitation maximum | Fluorescence maximum | Molar absorption coefficient | Quantum yield | pH sensitivity | Number of amino acids |
|---|---|---|---|---|---|---|
| MIG | 505 nm | 516 nm | 53,600 (505 nm) | 0.67 | pKa = 6.4 | 232 |

(9) Measurement of pH Sensitivity

The fluorescent protein was diluted with each of the following buffer solutions. The value of the absorption at 505 nm was determined, and thus the pH sensitivity thereof was measured. The pH levels of the buffer solutions are as follows.
pH 4 and 5: Acetate buffer
pH 6 and 11: Phosphate buffer
pH 7 and 8: HEPES buffer
pH 9 and 10: Glycine buffer The measurement results are shown in FIG. 3C.

Example 3

Isolation of Novel Fluorescent Protein Gene (MICy) from Coral (1) Extraction of Total RNA A fluorescent protein gene was isolated from coral emitting a fluorescence. *Acropora* sp. was used as a material. *Acropora* sp. was crushed with a hammer, and 15 ml of TRIZOL (reagent for RNA preparation/isolation) (GIBCO BRL) was then added to 5 g of the crushed *Acropora* sp. Thereafter, the obtained mixture was stirred and then centrifuged at 1,500×g for 10 minutes. Thereafter, 3 ml of chloroform was added to the obtained supernatant, and the mixture was then stirred for 15 seconds. Thereafter, the mixture was left at rest for 3 minutes. The resultant was then centrifuged at 7,500×g for 15 minutes. Thereafter, 7.5 ml of isopropanol was added to the obtained supernatant, and the mixture was then stirred for 15 seconds, followed by leaving the mixture at rest for 10 minutes. Thereafter, the resultant was centrifuged at 17,000×g for 10 minutes. The obtained supernatant was discarded, and 6 ml of 70% ethanol was added to the residue, followed by centrifugation at 17,000×g for 10 minutes. The obtained supernatant was discarded, and the precipitate was then dissolved in 200 μl of DEPC water. Total RNA dissolved in the DEPC water was 100 times diluted, and the values of O.D.260 and O.D.280 were then measured, so as to determine RNA concentration. As a result, 220 μg of total RNA was obtained.

(2) Synthesis of First Strand cDNA cDNA (33 μl) was synthesized from 5 μg of the total RNA, using a kit for synthesizing first strand cDNA "Ready To Go" (Amersham Pharmacia).

(3) Degenerated PCR

3 μl of the synthesized first strand cDNA (33 μl) was used as a template to carry out PCR. Primers were produced by making comparison among the amino acid sequences of known fluorescent proteins, extracting similar portions, and converting them to nucleotide sequences. Primers used:

```
                                     (SEQ ID NO: 15)
        5'-GAAGGRTGYGTCAAYGGRCAY-3'  (primer 1)

(SEQ ID NO: 16)
        5'-ACVGGDCCATYDGVAAGAAARTT-3' (primer 2)
```

R represents A or G; Y represents C or T; V represents A, C, or G; D represents A, G, or T
Composition of PCR reaction solution:

| | |
|---|---|
| Template (first strand cDNA) | 3 μl |
| X10 TAQ (polymerase) buffer | 5 μl |
| 2.5 mM dNTPs | 4 μl |
| 100 μM primer 1 | 1 μl |
| 100 μM primer 2 | 1 μl |

| MILLI-Q (reagent grade water) | 35 µl |
|---|---|
| TAQ polymerase (5 U/µl) | 1 µl |

PCR reaction conditions:
94° C. ×1 min (PAD)
94° C. ×30 sec (denaturation)
52° C. ×30 sec (annealing of primers to template)
72° C. ×1 min (primer elongation)

A cycle consisting of the aforementioned 3 steps was repeated 30 times. The annealing temperature was decreased by 0.3° C. for every cycle. The annealing temperature was 43° C. at the time of the 30$^{th}$ cycle.
72° C.×7 min (final elongation)
4° C. (maintenance)

Using 1 µl of the amplified product obtained in the first PCR reaction as a template, PCR was carried out again under the same above conditions. A band with an estimated size of 350 bp was cut out via agarose gel electrophoresis, and it was then purified.

(4) Subcloning and Sequencing

The purified DNA fragment was ligated to a pT7-blue vector (Novagen). Escherichia coli (TG1) was transformed therewith, and it was then subjected to blue white selection. Plasmid DNA was purified from white colonies of Escherichia coli, and the nucleotide sequence of the inserted DNA fragment was determined using a DNA sequencer. Thereafter, the obtained nucleotide sequence was compared with the nucleotide sequences of other fluorescent protein genes, so as to determine whether the nucleotide sequence of the DNA fragment was derived from a fluorescent protein. With regard to those that were determined to be a part of the fluorescent protein genes, the full-length genes were cloned by the 5'-RACE method and the 3'-RACE method.

(5) 5'-RACE Method

In order to determine the nucleotide sequence on the 5'-side of the DNA fragment obtained by the degenerated PCR, the 5'-RACE method was applied using 5'-RACE System for Rapid Amplification of cDNA Ends, Version 2.0 (GIBCO BRL). 3 µg of the total RNA prepared in (1) above was used as a template. The following primers were used in the first amplification of dC-tailed cDNA:

```
                                        (SEQ ID NO: 17)
5'-GGCCACGCGTCGACTAGTACGGGIIGGGIIGGGIIG-3'
(primer 3);
and (SEQ ID NO: 27)
5'- TAGAAATGACCTTTCATATGACATTC -3' (primer 4).
```

Herein, I represents inosine.

The following primers were used in the second amplification:

```
                                        (SEQ ID NO: 19)
5'-GGCCACGCGTCGACTAGTAC-3' (primer 5);
and (SEQ ID NO: 28)
5'-TCTGTTTCCATATTGAAAGGCTG-3' (primer 6).
```

PCR reaction conditions were applied in accordance with protocols attached to the kit.

The amplified 500-bp band was cut out of the gel via agarose gel electrophoresis and then purified. The purified DNA fragment was ligated to a pT7-blue vector (Novagen).

Escherichia coli (TG1) was transformed therewith, and it was then subjected to blue white selection. Plasmid DNA was purified from white colonies of Escherichia coli, and the nucleotide sequence of the inserted DNA fragment was determined using a DNA sequencer.

(6) 3'-RACE Method

The nucleotide sequence on the 3'-side of the DNA fragment obtained by the degenerated PCR was obtained by PCR using a primer prepared based on the information obtained by determination of the nucleotide sequence in (4) above and an oligo dT primer. 3 µl of the first strand cDNA prepared in (2) above was used as a template. The prepared primer was

```
                                        (SEQ ID NO: 29)
5'-ATGGTGTCTTATTCAAAGCAAGGCATCGCACA-3' (primer 7).
```

Composition of PCR reaction solution:

| Template (first strand cDNA) | 3 µl |
|---|---|
| X10 TAQ (polymerase) buffer | 5 µl |
| 2.5 mM dNTPs | 4 µl |
| 20 µM primer 7 | 1 µl |
| 10 µM oligo dT primer | 1 µl |
| MILLI-Q (reagent grade water) | 35 µl |
| TAQ polymerase (5 U/µl) | 1 µl |

PCR reaction conditions:
94° C. ×1 minute (PAD)
94° C. ×30 seconds (denaturation)
55° C. ×30 seconds (annealing of primers to template)
72° C. ×1 minute (primer elongation)
4° C. (maintenance)

The amplified band with a length of 900 bp was cut out of the gel via agarose gel electrophoresis and then purified. The purified DNA fragment was ligated to a pT7-blue vector (Novagen). Escherichia coli (TG1) was transformed therewith, and it was then subjected to blue white selection. Plasmid DNA was purified from white colonies of Escherichia coli, and the nucleotide sequence of the inserted DNA fragment was determined using a DNA sequencer.

The obtained full-length nucleotide sequence is shown in SEQ ID NO: 6 of the sequence listing, and the obtained full-length amino acid sequence is shown in SEQ ID NO: 5 thereof. This clone was named MiCy.

(7) Expression of Protein in Escherichia coli

Using a primer produced with a portion corresponding to the N-terminus of the obtained full-length nucleotide sequence of the protein and an oligo dT primer, PCR was carried out employing the first strand cDNA prepared in (2) above as a template.

Primer used:

```
                                        (SEQ ID NO: 30)
5'-CGGGATCCGACCATGGTGTCTTATTCAAAGCAAGGCATCGCACA-3'
(primer 8)
```

Composition of PCR reaction solution:

| Template (first strand cDNA) | 3 µl |
|---|---|
| X10 PYROBEST (polymerase) buffer | 5 µl |
| 2.5 mM dNTPs | 4 µl |
| 20 µM primer 8 | 1 µl |

-continued

| | |
|---|---|
| 20 µM oligo dT primer | 1 µl |
| MILLI-Q (reagent grade water) | 35 µl |
| PYROBEST polymerase (5 U/µl) | 1 µl |

PCR reaction conditions:
94° C. ×1 minute (PAD)
94° C. ×30 seconds (denaturation)
55° C. ×30 seconds (annealing of primers to template)
72° C. ×1 minute (primer elongation)
4° C. (maintenance)

The amplified band with a length of 900 bp was cut out of the gel via agarose gel electrophoresis and then purified. The purified DNA fragment was subcloned into the BamHI-EcoRI site of a pRSET vector (Invitrogen), and it was then allowed to express in *Escherichia coli* (JM109-DE3). The expressed protein was constructed such that His-tag was attached to the N-terminus thereof, and thus it was purified with Ni-Agarose gel (QIAGEN). Purification was carried out in accordance with the attached protocols. Subsequently, the properties of the purified protein were analyzed.

(8) Analysis of Fluorescence Properties

Figure 4:
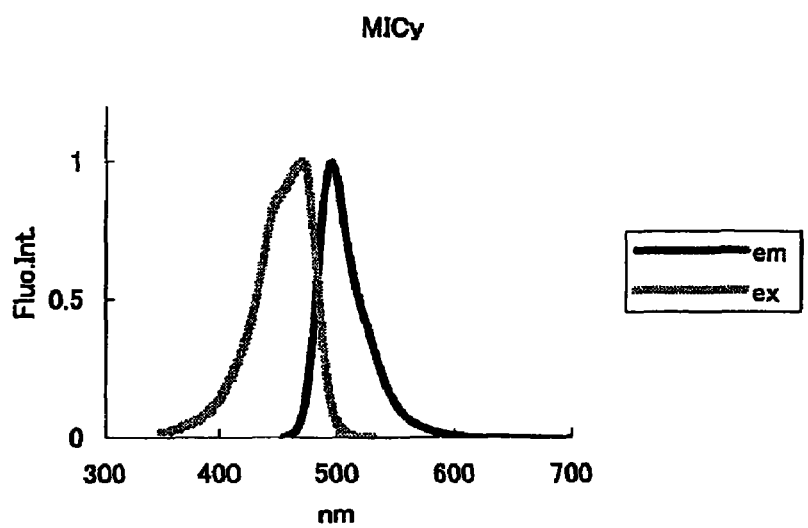
FIG. 4 shows the fluorescence spectrum and excitation spectrum of the fluorescent protein (MICy) of the present invention derived from *Acropora* sp. (FIG. A), the absorption spectrum of the fluorescent protein (MICy) (FIG. B), and the pH sensitivity of the fluorescent protein (MICy) (FIG. C). In FIG. C, the horizontal axis represents pH value, and the longitudinal axis represents absorbance.
Figure 4:
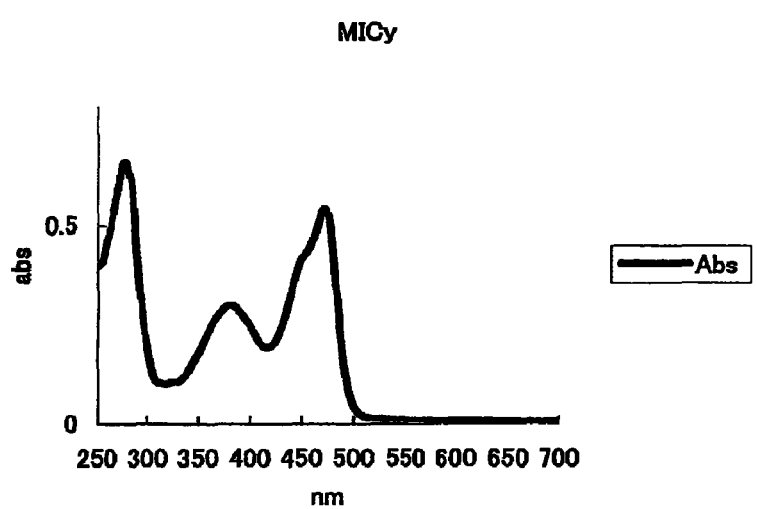
Figure 4:
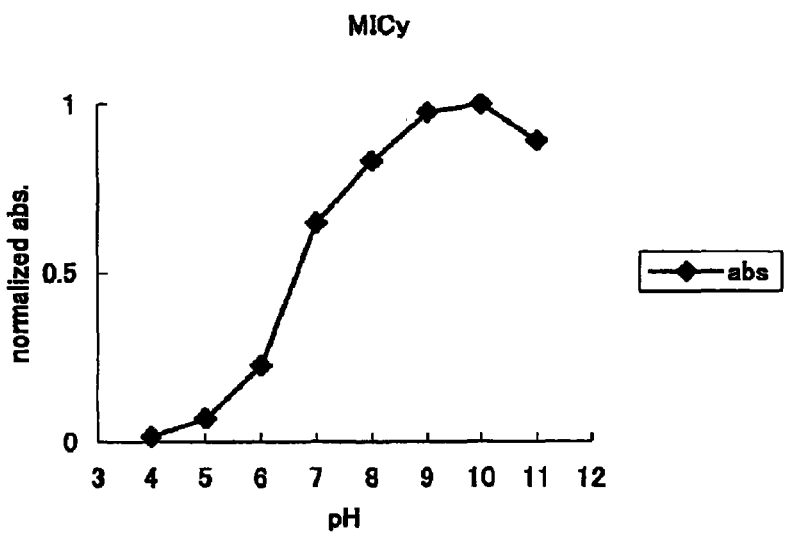

Using a solution comprising 20 µM fluorescent protein (MICy), 150 mM KCl, and 50 mM HEPES (pH 7.4), the absorption spectrum of the protein was measured (FIG. 4B). Thereafter, the molar absorption coefficient of the protein was calculated from the value of the peak (472 nm) of the spectrum. The fluorescent protein was diluted with the above buffer solution such that the absorption at 440 nm became 0.001. Its fluorescence spectrum by exciting at 440 nm and its excitation spectrum by a fluorescence at 540 nm were measured (FIG. 4A). Likewise, EGFP (CLONTECH) was diluted such that the absorption at 440 nm became 0.001, and its fluorescence spectrum was measured. Setting the quantum yield of EGFP to 0.6, the quantum yield of the cloned fluorescent protein was obtained. The measurement results are shown in Table 3.

TABLE 3

| | Excitation maximum | Fluorescence maximum | Molar absorption coefficient | Quantum yield | pH sensitivity | Number of amino acids |
|---|---|---|---|---|---|---|
| MICy | 472 nm | 496 nm | 27,250 (472 nm) | 0.90 | pKa = 6.6 | 232 |

(9) Measurement of pH Sensitivity

The fluorescent protein was diluted with each of the following buffer solutions. The value of the absorption at 472 nm was determined, and thus the pH sensitivity thereof was measured. The pH levels of the buffer solutions are as follows.
pH 4 and 5: Acetate buffer
pH 6 and 11: Phosphate buffer
pH 7 and 8: HEPES buffer
pH 9 and 10: Glycine buffer The measurement results are shown in FIG. 4C.

(10) Production of pH Tolerance Mutant MiCy2 of MICy

Figure 5:
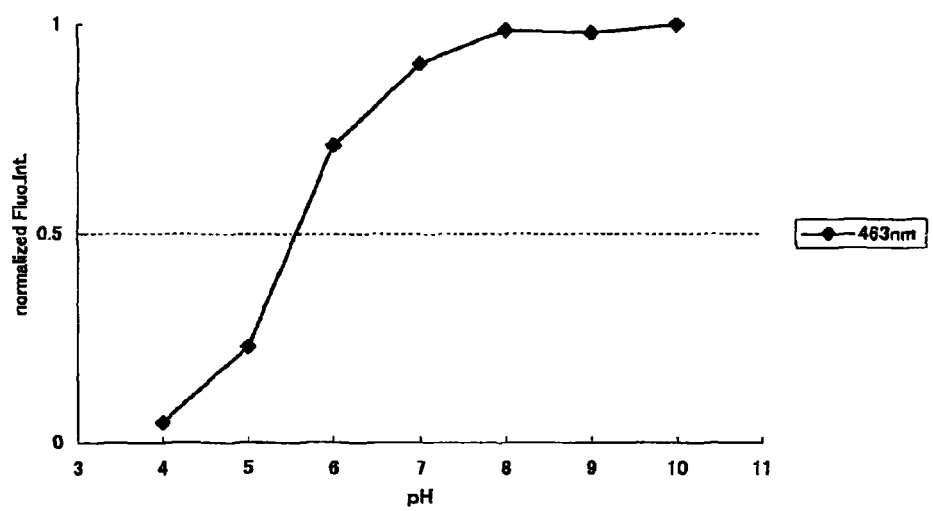
FIG. 5 shows the pH sensitivity of the fluorescent protein (MiCy2) of the present invention (FIG. A), and the excitation and fluorescence spectra thereof (FIG. B).
Figure 5:
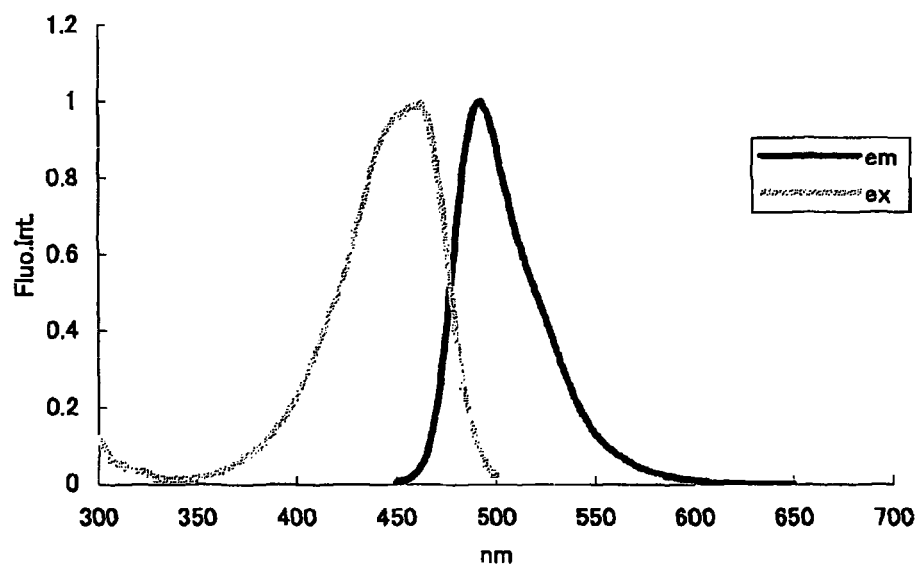

Glutamine (Q) at position 166 of MICy was substituted with histidine (H), so as to produce MiCy2 having stronger fluorescence intensity on the acidic side than that of MICy (the amino acid sequence of which is shown in SEQ ID NO: 7, and the nucleotide sequence of which is shown in SEQ ID NO: 8). Specifically, pKa of 6.6 was decreased to 5.6, the fluorescence peak was found to be 493 nm, and the excitation peak was found to be 462 nm (FIGS. 5A and 5B).

Example 4

Isolation of Novel Fluorescent Protein Gene (COR) from Stony Coral, and Analysis of Fluorescence Properties Thereof (1) Extraction of Total RNA A fluorescent protein gene was isolated from coral. *Montipora* sp. was used as a material. A frozen *Montipora* sp. was crushed in a mortar, and 7.5 ml of TRIZOL (reagent for RNA preparation/isolation) (GIBCO BRL) was then added to 2 g (wet weight) of the crushed *Montipora* sp. Thereafter, the obtained mixture was homogenized and then centrifuged at 1,500×g for 10 minutes. Thereafter, 1.5 ml of chloroform was added to the obtained supernatant, and the mixture was then stirred for 15 seconds. Thereafter, the mixture was left at rest for 3 minutes. The resultant was then centrifuged at 7,500×g for 15 minutes. Thereafter, 3.75 ml of isopropanol was added to the obtained supernatant, and the mixture was then stirred for 15 seconds, followed by leaving the mixture at rest for 10 minutes. Thereafter, the resultant was centrifuged at 17,000×g for 10 minutes. The obtained supernatant was discarded, and 6 ml of 70% ethanol was added to the residue, followed by centrifugation at 17,000×g for 10 minutes. The obtained supernatant was discarded, and the precipitate was then dissolved in 200 µl of DEPC water. Total RNA dissolved in the DEPC water was 100 times diluted, and the values of O.D.260 and O.D.280 were then measured, so as to determine RNA concentration. As a result, 22 µg of total RNA was obtained.

(2) Synthesis of First Strand cDNA cDNA (33 µl) was synthesized from 4 µg of the total RNA, using a kit for synthesizing first strand cDNA "Ready To Go" (Amersham Pharmacia).

(3) Degenerated PCR

3 µl of the synthesized first strand cDNA (33 µl) was used as a template to carry out PCR.

Primers were produced by making comparison among the amino acid sequences of known fluorescent proteins, extracting similar portions, and converting them to nucleotide sequences.

Primers used:

```
                                            (SEQ ID NO: 15)
5'-GAAGGRTGYGTCAAYGGRCAY-3' (primer 1)

(SEQ ID NO: 16)
5'-ACVGGDCCATYDGVAAGAAARTT-3' (primer 2)
```

I represents inosine; R represents A or G; Y represents C or T; V represents A, C, or G; D represents A, G, or T; S represents C or G; H represents A, T, or C Composition of PCR reaction solution:

| | |
|---|---|
| Template (first strand cDNA) | 3 µl |
| X10 TAQ (polymerase) buffer | 5 µl |
| 2.5 mM dNTPs | 4 µl |
| 100 µM primer 1 | 1 µl |
| 100 µM primer 2 | 1 µl |
| MILLI-Q (reagent grade water) | 35 µl |
| TAQ polymerase (5 U/µl) | 1 µl |

PCR reaction conditions:
94° C. ×1 min (PAD)
94° C. ×30 sec (denaturation)
52° C. ×30 sec (annealing of primers to template)
72° C. ×1 minute (primer elongation)
4° C. (maintenance)

Using 1 μl of the amplified product obtained in the first PCR reaction as a template, PCR was carried out again under the same above conditions. A 350-bp fragment was cut out via agarose gel electrophoresis, and it was then purified.

(4) Subcloning and Sequencing

The purified DNA fragment was ligated to a pT7-blue vector (Novagen). *Escherichia coli* (TG1) was transformed therewith, and it was then subjected to blue white selection. Plasmid DNA was purified from white colonies of *Escherichia coli*, and the nucleotide sequence of the inserted DNA fragment was determined using a DNA sequencer. Thereafter, the obtained nucleotide sequence was compared with the nucleotide sequences of other fluorescent protein genes, so as to determine whether the nucleotide sequence of the DNA fragment was derived from a fluorescent protein. With regard to those that were determined to be a part of the fluorescent protein genes, the full-length genes were cloned by the 5'-RACE method and the 3'-RACE method.

(5) 5'-RACE Method

In order to determine the nucleotide sequence on the 5'-side of the DNA fragment obtained by the degenerated PCR, the 5'-RACE method was applied using 5'-RACE System for Rapid Amplification of cDNA Ends, Version 2.0 (GIBCO BRL). 5 μg of the total RNA prepared in (1) above was used as a template.

The following primers were used in the first amplification of dC-tailed cDNA:

```
                                          (SEQ ID NO: 17)
5'-GGCCACGCGTCGACTAGTACGGGIIGGGIIGGGIIG-3'
(primer 3);
and (SEQ ID NO: 18)
5'-CCATCTTCAAAGAGAAAAGACCTTT-3' (primer 4).
```

Herein, I represents inosine.

The following primers were used in the second amplification:

```
                                          (SEQ ID NO: 19)
5'-GGCCACGCGTCGACTAGTAC-3' (primer 5);
and (SEQ ID NO: 20)
5'-CATGAGTTCTTGAAATAGTCAAC-3' (primer 6).
```

PCR reaction conditions were applied in accordance with protocols attached to the kit.

The amplified 350-bp band was cut out of the gel via agarose gel electrophoresis and then purified. The purified DNA fragment was ligated to a pT7-blue vector (Novagen). *Escherichia coli* (TG1) was transformed therewith, and it was then subjected to blue white selection. Plasmid DNA was purified from white colonies of *Escherichia coli*, and the nucleotide sequence of the inserted DNA fragment was determined using a DNA sequencer.

(6) 3'-RACE Method

The nucleotide sequence on the 3'-side of the DNA fragment obtained by the degenerated PCR was obtained by PCR using a primer prepared based on the information obtained by determination of the nucleotide sequence in (4) above and an oligo dT primer. 3 μl of the first strand cDNA prepared in (2) above was used as a template. The prepared primer was 5'-ATGGCTCTTTCAAAGCACGGTC-3' (primer 7) (SEQ ID NO: 31).

Composition of PCR reaction solution:

| | |
|---|---|
| Template (first strand cDNA) | 3 μl |
| X10 TAQ (polymerase) buffer | 5 μl |
| 2.5 mM dNTPs | 4 μl |
| 20 μM primer 7 | 1 μl |
| 10 μM oligo dT primer | 1 μl |
| MILLI-Q (reagent grade water) | 35 μl |
| TAQ polymerase (5 U/μl) | 1 μl |

PCR reaction conditions:
94° C. ×1 minute (PAD)
94° C. ×30 seconds (denaturation)
52° C. ×30 seconds (annealing of primers to template)
72° C. ×1 minute (primer elongation)
4° C. (maintenance)

The amplified band with a length of approximately 1,000 bp was cut out of the gel via agarose gel electrophoresis and then purified. The purified DNA fragment was ligated to a pT7-blue vector (Novagen). *Escherichia coli* (TG1) was transformed therewith, and it was then subjected to blue white selection. Plasmid DNA was purified from white colonies of *Escherichia coli*, and the nucleotide sequence of the inserted DNA fragment was determined using a DNA sequencer.

The obtained full-length nucleotide sequence is shown in SEQ ID NO: 10 of the sequence listing, and the obtained full-length amino acid sequence is shown in SEQ ID NO: 9 thereof. This clone was named COR.

(7) Expression of Protein in *Escherichia coli*

Based on the obtained full-length nucleotide sequence, a primer was produced with a portion corresponding to the N-terminus of the protein. An oligo dT primer was used as a primer corresponding to the C-terminal side thereof. Thereafter, using such primers, PCR was carried out employing the first strand cDNA prepared in (2) above as a template.

Primer used:

```
                                          (SEQ ID NO: 32)
5'-GGGGGATCCGACCATGGCTCTTTCAAAGCACGGTC-3'
(primer 8)
```

Composition of PCR reaction solution:

| | |
|---|---|
| Template (first strand cDNA) | 3 μl |
| X10 PYROBEST (polymerase) buffer | 5 μl |
| 2.5 mM dNTPs | 4 μl |
| 100 μM primer 8 | 1 μl |
| 100 μM oligo dT primer | 1 μl |
| MILLI-Q (reagent grade water) | 35 μl |
| PYROBEST polymerase (5 U/μl) | 1 μl |

PCR reaction conditions:
94° C. ×1 minute (PAD)
94° C. ×30 seconds (denaturation)
52° C. ×30 seconds (annealing of primers to template)
72° C. ×1 minute (primer elongation)
A cycle consisting of the aforementioned 3 steps was repeated 30 times.
72° C.×7 minutes (final elongation)
4° C. (maintenance)

The amplified band with a length of approximately 1,000 bp was cut out of the gel via agarose gel electrophoresis and then purified. The purified DNA fragment was subcloned into the BamHI-EcoRI site of a pRSET vector (Invitrogen), and it was then allowed to express in *Escherichia coli* (JM109-

DE3). The expressed protein was constructed such that His-tag was attached to the N-terminus thereof, and thus it was purified with Ni-Agarose gel (QIAGEN). Purification was carried out in accordance with the attached protocols. Subsequently, the properties of the purified protein were analyzed.

(8) Analysis of Fluorescence Properties

Figure 6:
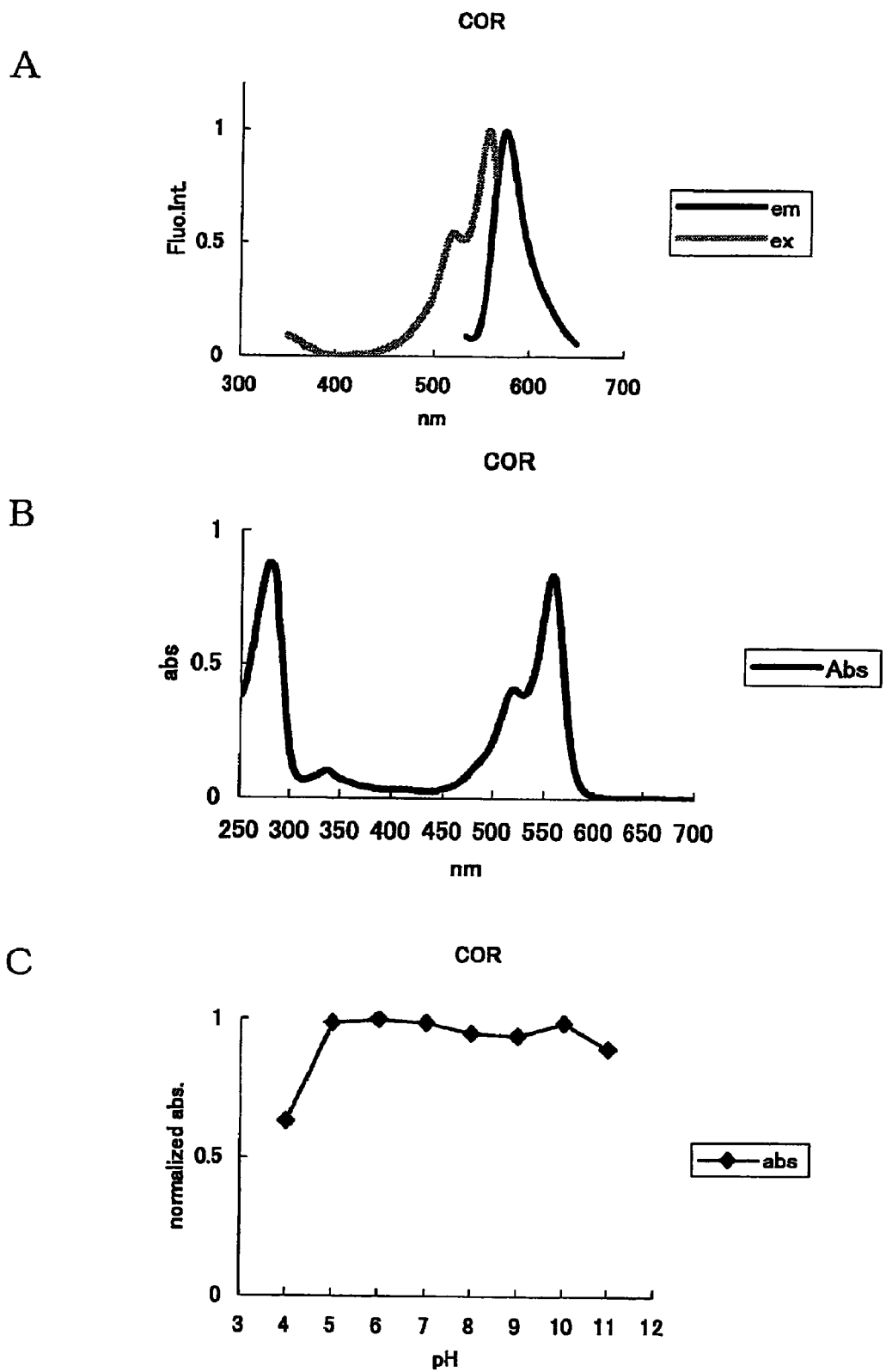
FIG. 6 shows the fluorescence spectrum and excitation spectrum of the fluorescent protein (COR) of the present invention derived from *Montipora* sp. (FIG. A), the absorption spectrum of the fluorescent protein (COR) (FIG. B), and the pH sensitivity of the fluorescent protein (COR) (FIG. C). In FIG. C, the horizontal axis represents pH value, and the longitudinal axis represents absorbance.

Using a solution comprising 20 μM fluorescent protein (COR), 150 mM KCl, and 50 mM HEPES (pH 7.5), the absorption spectrum of the protein was measured (FIG. 6B). Thereafter, the molar absorption coefficient of the protein was calculated from the value of the peak (557 nm) of the spectrum. The fluorescent protein was diluted with the above buffer solution such that the absorption at 520 nm became 0.002. Its fluorescence spectrum by exciting at 520 nm and its excitation spectrum by a fluorescence at 600 nm were measured (FIG. 6A). Likewise, DsRed2 (CLONTECH) was diluted such that the absorption at 520 nm became 0.002, and its fluorescence spectrum was measured. Setting the quantum yield of DsRed2 to 0.55, the quantum yield of the cloned fluorescent protein was obtained. The measurement results are shown in Table 4.

TABLE 4

|  | Excitation maximum | Fluorescence maximum | Molar absorption coefficient | Quantum yield | pH sensitivity | Number of amino acids |
| --- | --- | --- | --- | --- | --- | --- |
| COR | 557 nm | 574 nm | 41,750 (557 nm) | 0.41 | pKa < 4.0 | 232 |

(9) Measurement of pH Sensitivity

The fluorescent protein was diluted with each of the following buffer solutions to the same concentration. The value of the absorption at 557 nm was determined, and thus the pH sensitivity thereof was measured. The pH levels of the buffer solutions are as follows.
pH 4 and 5: Acetate buffer
pH 6 and 11: Phosphate buffer
pH 7 and 8: HEPES buffer
pH 9 and 10: Glycine buffer The measurement results are shown in FIG. 6C.

Example 5

Isolation of Novel Chromoprotein Gene from Sea Anemone, and Analysis of 1 Light-absorbing Properties Thereof (1) Extraction of Total RNA A chromoprotein gene was isolated from sea anemone. A single body of *Actinia equina* presenting a red color was used as a material. A frozen *Actinia equina* was crushed in a mortar, and 7.5 ml of TRIZOL (reagent for RNA preparation/isolation) (GIBCO BRL) was then added to 1 g (wet weight) of the crushed *Actinia equina*. Thereafter, the obtained mixture was homogenized and then centrifuged at 1,500×g for 10 minutes. Thereafter, 1.5 ml of chloroform was added to the obtained supernatant, and the mixture was then stirred for 15 seconds. Thereafter, the mixture was left at rest for 3 minutes. The resultant was then centrifuged at 7,500×g for 15 minutes. Thereafter, 3.75 ml of isopropanol was added to the obtained supernatant, and the mixture was then stirred for 15 seconds, followed by leaving the mixture at rest for 10 minutes. Thereafter, the resultant was centrifuged at 17,000×g for 10 minutes. The obtained supernatant was discarded, and 6 ml of 70% ethanol was added to the residue, followed by centrifugation at 17,000×g for 10 minutes. The obtained supernatant was discarded, and the precipitate was then dissolved in 200 μl of DEPC water. Total RNA dissolved in the DEPC water was 100 times diluted, and the values of O.D.260 and O.D.280 were then measured, so as to determine RNA concentration. As a result, 1.2 mg of total RNA was obtained.

(2) Synthesis of First Strand cDNA cDNA (33 μl) was synthesized from 4 μg of the total RNA, using a kit for synthesizing first strand cDNA "Ready To Go" (Amersham Pharmacia).

(3) Degenerated PCR

3 μl of the synthesized first strand cDNA (33 μl) was used as a template to carry out PCR.

Primers were produced by making comparison among the amino acid sequences of known fluorescent proteins, extracting similar portions, and converting them to nucleotide sequences.

Primers used:

```
                                    (SEQ ID NO: 33)
5'- GGI WSB GTI AAY GGV CAY DAN TT -3' (primer 1);
and (SEQ ID NO: 34)
5'- GTC ITC TTY TGC ACI ACI GGI CCA TYD GVA GGA
AA -3' (primer 2).
```

I represents inosine; R represents A or G; Y represents C or T; V represents A, C, or G; D represents A, G, or T; S represents C or G; H represents A, T, or C Composition of PCR reaction solution:

| | |
| --- | --- |
| Template (first strand cDNA) | 3 μl |
| X10 TAQ (polymerase) buffer | 5 μl |
| 2.5 mM dNTPs | 4 μl |
| 100 μM primer 1 | 1 μl |
| 100 μM primer 2 | 1 μl |
| MILLI-Q (reagent grade water) | 35 μl |
| TAQ polymerase (5 U/μl) | 1 μl |

PCR reaction conditions:
94° C. ×1 minute (PAD)
94° C. ×30 seconds (denaturation)
58° C. ×30 seconds (annealing of primers to template)
72° C. ×1 minute (primer elongation)
4° C. (maintenance)

Using 1 μl of the amplified product obtained in the first PCR reaction as a template, PCR was carried out again under the same above conditions. A 350-bp fragment was cut out via agarose gel electrophoresis, and it was then purified.

(4) Subcloning and Sequencing

The purified DNA fragment was ligated to a pT7-blue vector (Novagen). *Escherichia coli* (TG1) was transformed therewith, and it was then subjected to blue white selection. Plasmid DNA was purified from white colonies of *Escherichia coli*, and the nucleotide sequence of the inserted DNA fragment was determined using a DNA sequencer. Thereafter, the obtained nucleotide sequence was compared with the nucleotide sequences of other fluorescent protein genes, so as to determine whether the nucleotide sequence of the DNA fragment was derived from a fluorescent protein. With regard to those that were determined to be a part of the chromoprotein genes, the full-length genes were cloned by the 5'-RACE method and the 3'-RACE method.

(5) 5'-RACE Method

In order to determine the nucleotide sequence on the 5'-side of the DNA fragment obtained by the degenerated PCR, the 5'-RACE method was applied using 5'-RACE System for Rapid Amplification of cDNA Ends, Version 2.0 (GIBCO BRL). 4 µg of the total RNA prepared in (1) above was used as a template.

The following primers were used in the first amplification of dC-tailed cDNA derived from the red color individual:

```
                                          (SEQ ID NO: 17)
5'-GGCCACGCGTCGACTAGTACGGGIIGGGIIGGGIIG-3'
(primer 3);
and (SEQ ID NO: 35)
5'-CCT TGA AAA TAA AGC TAT CT-3' (primer 4).
```

Herein, I represents inosine.

The following primers were used in the second amplification:

```
                                          (SEQ ID NO: 19)
5'-GGCCACGCGTCGACTAGTAC-3' (primer 5);
and (SEQ ID NO: 36)
5'-CCC TGT ATG CTT GTG TCC TG-3' (primer 6).
```

PCR reaction conditions were applied in accordance with protocols attached to the kit.

The amplified 200-bp band was cut out of the gel via agarose gel electrophoresis and then purified. The purified DNA fragment was ligated to a pT7-blue vector (Novagen). *Escherichia coli* (TG1) was transformed therewith, and it was then subjected to blue white selection. Plasmid DNA was purified from white colonies of *Escherichia coli*, and the nucleotide sequence of the inserted DNA fragment was determined using a DNA sequencer.

(6) Determination of Full Length Nucleotide Sequence, and Expression of Protein in *Escherichia coli*

A primer was produced with a portion corresponding to the N-terminus of the protein obtained in (5) above. An oligo dT primer was used as a primer corresponding to the C-terminal side thereof. Thereafter, using such primers, PCR was carried out employing the first strand cDNA prepared in (2) above as a template.

Primer used:

```
                                          (SEQ ID NO: 37)
5'-CCC GGA TCC GAC CAT GGT GTC TTC ATT GGT AAG
GAA-3' (primer 7)
```

Composition of PCR reaction solution:

| | |
|---|---|
| Template (first strand cDNA) | 3 µl |
| X10 PYROBEST (polymerase) buffer | 5 µl |
| 2.5 mM dNTPs | 4 µl |
| 100 µM primer 8 | 1 µl |
| 100 µM oligo dT primer | 1 µl |
| MILLI-Q (reagent grade water) | 35 µl |
| PYROBEST polymerase (5 U/µl) | 1 µl |

PCR reaction conditions:
94° C. ×1 minute (PAD)
94° C. ×30 seconds (denaturation)
52° C. ×30 seconds (annealing of primers to template)
72° C. ×1 minute (primer elongation)
4° C. (maintenance)

The amplified band with a length of approximately 900 bp was cut out of the gel via agarose gel electrophoresis and then purified. The purified DNA fragment was subcloned into the BamHI-EcoRI site of a pRSET vector (Invitrogen), and it was then allowed to express in *Escherichia coli* (JM109-DE3). In addition, the plasmid was recovered, and the full length nucleotide sequence that had been inserted was determined. The clone was named Ume. The full length nucleotide sequence thereof and the full length amino acid sequence thereof are shown in SEQ ID NOS: 12 and 11 of the sequence listing, respectively. The expressed protein was constructed such that His-tag was attached to the N-terminus thereof, and thus it was purified with Ni-Agarose gel (QIAGEN). Purification was carried out in accordance with the attached protocols. Subsequently, the properties of the purified protein were analyzed.

(7) Analysis of Light-Absorbing Properties

Figure 7:
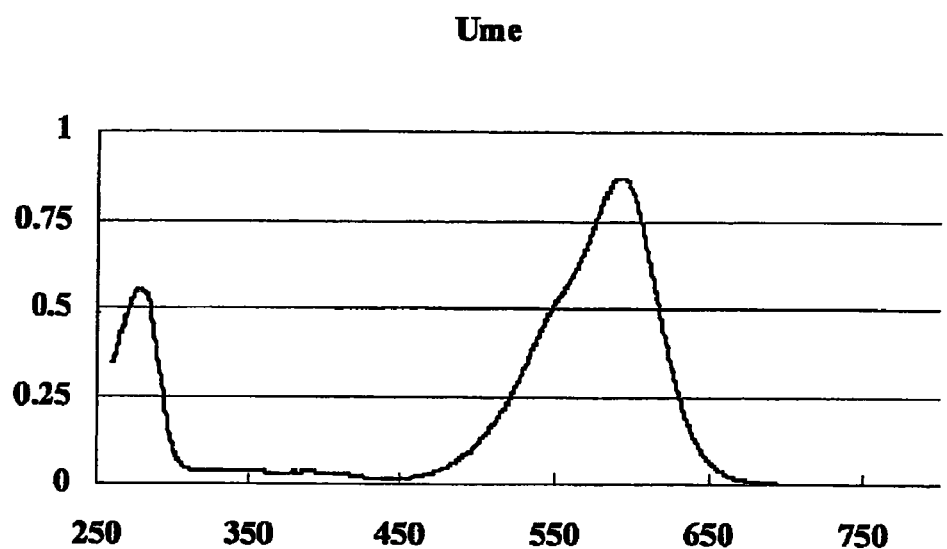
FIG. 7 shows the results obtained by the measurement of the absorption spectrum (pH 7.9) of the chromoprotein (Ume) of the present invention derived from *Actinia equina* (FIG. A), and the pH sensitivity of the absorption maximum of the chromoprotein (Ume) (FIG. B). In FIG. A, the horizontal axis represents the wavelength of an absorbed light, and the longitudinal axis represents absorbance. In FIG. B, the horizontal axis represents pH value, and the longitudinal axis represents absorbance.
Figure 7:
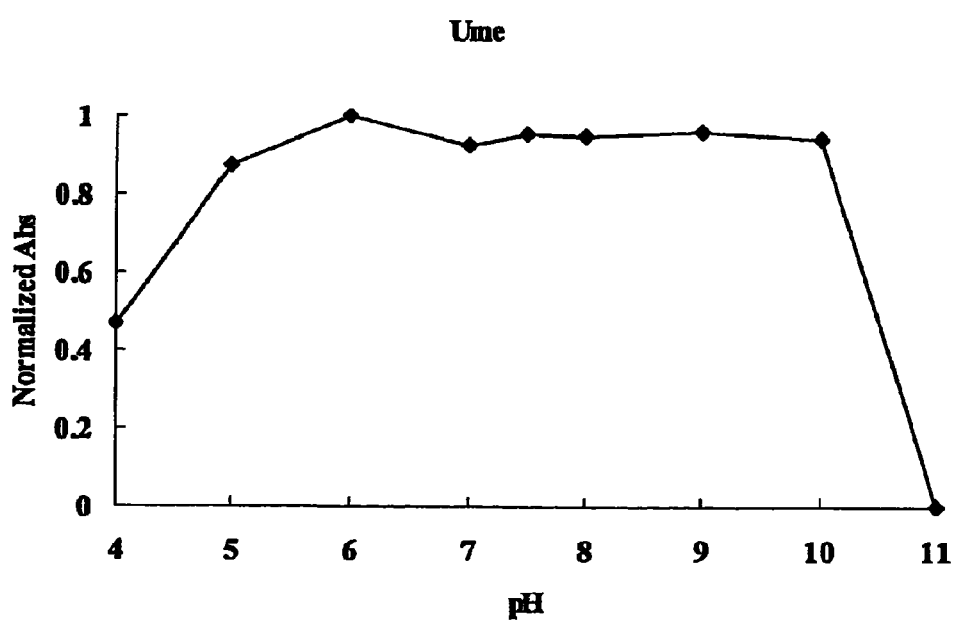

Using a solution comprising 10 µM chromoprotein (Ume) and 50 mM HEPES (pH 7.9), the absorption spectrum of the protein was measured. Thereafter, the molar absorption coefficient of the protein was calculated from the value of the peak of the spectrum. In the chromoprotein (Ume) derived from the red color individual, the absorption peak was observed at 592 nm (FIG. 7A). The measurement results are shown in Table 5.

TABLE 5

| | Absorption maximum | Molar absorption coefficient | pH sensitivity | Number of amino acids |
|---|---|---|---|---|
| Ume | 592 nm | 87,000 (592 nm) | Stable between pH 5 and pH 10 | 232 |

(9) Measurement of pH Sensitivity

The absorption spectrum of the protein was measured in each of the following 50 mM buffer solutions (FIG. 7B). The pH levels of the buffer solutions are as follows.
pH 4 and 5: Acetate buffer
pH 6: Phosphate buffer
pH 7 and 8: HEPES buffer
pH 9 and 10: Glycine buffer The peak value was stable in the range between pH 5 and 10.

Example 6

Isolation of Novel Fluorescent Protein Gene from Coral (*Lobophytum crassum*)

(1) Extraction of Total RNA

A fluorescent protein gene was isolated from coral emitting a fluorescence. *Lobophytum crassum* was used as a material. This coral was crushed with a hammer, and 7.5 ml of TRIZOL (reagent for RNA preparation/isolation) (GIBCO BRL) was then added to 4 g (wet weight) of the crushed *Lobophytum crassum*. Thereafter, the obtained mixture was stirred and then centrifuged at 1,500×g for 10 minutes. Thereafter, 1.5 ml of chloroform was added to the obtained supernatant, and the mixture was then stirred for 15 seconds. Thereafter, the mixture was left at rest for 3 minutes. The resultant was then centrifuged at 7,500×g for 15 minutes. Thereafter, 3.75 ml of isopropanol was added to the obtained supernatant, and the mixture was then stirred for 15 seconds, followed by leaving the mixture at rest for 10 minutes. Thereafter, the resultant was centrifuged at 17,000×g for 10 minutes. The obtained supernatant was discarded, and 6 ml of 70% ethanol was added to the residue, followed by centrifugation at 17,000×g for 10 minutes. The obtained supernatant was discarded, and the precipitate was then dissolved in 200 µl of DEPC water.

Total RNA dissolved in the DEPC water was 100 times diluted, and the values of O.D.260 and O.D.280 were then measured, so as to determine RNA concentration. As a result, 390 μg of total RNA was obtained.

(2) Synthesis of First Strand cDNA cDNA (33 μl) was synthesized from 3 μg of the total RNA, using a kit for synthesizing first strand cDNA "Ready To Go" (Amersham Pharmacia).

(3) Degenerated PCR

3 μl of the synthesized first strand cDNA (33 μl) was used as a template to carry out PCR. Primers were produced by making comparison among the amino acid sequences of known fluorescent proteins, extracting similar portions, and converting them to nucleotide sequences.

Primers used:

```
                                          (SEQ ID NO: 38)
5'-GRR AGG IWS BGT HAA YGG VCA-3' (Primer 1);
and (SEQ ID NO: 39)
5'-AACTGGAAGAATTCGCGGCCGCAGGAA-3' (Primer 2).
```

R represents A or G; Y represents C or T; V represents A, C, or G; D represents A, G, or T Composition of PCR reaction solution:

| | |
|---|---|
| Template (first strand cDNA) | 3 μl |
| X10 TAQ (polymerase) buffer | 5 μl |
| 2.5 mM dNTPs | 4 μl |
| 100 μM primer 1 | 1 μl |
| 100 μM primer 2 | 1 μl |
| MILLI-Q (reagent grade water) | 35 μl |
| TAQ polymerase (5 U/μl) | 1 μl |

PCR reaction conditions:
94° C. ×1 minute (PAD)
94° C. ×30 seconds (denaturation)
52° C. ×30 seconds (annealing of primers to template)
72° C. ×1 minute (primer elongation)
72° C. ×7 minutes (final elongation)
4° C. (maintenance)

Using 1 μl of the amplified product obtained in the first PCR reaction as a template, PCR was carried out again under the same above temperature conditions. As primers, the following primers were used:

```
                                          (SEQ ID NO: 38)
5'-GRR AGG IWS BGT HAA YGG VCA-3' (Primer 1);
and (SEQ ID NO: 40)
5'-GTC ITC TTY TGC ACI ACI GGI CCA TYD GVA GGA AA-3' (Primer 3).
```

A band with an estimated size of 350 bp was cut out via agarose gel electrophoresis, and it was then purified.

(4) Subcloning and Sequencing

The purified DNA fragment was ligated to a pT7-blue vector (Novagen). Escherichia coli (TG1) was transformed therewith, and it was then subjected to blue white selection. Plasmid DNA was purified from white colonies of Escherichia coli, and the nucleotide sequence of the inserted DNA fragment was determined using a DNA sequencer. Thereafter, the obtained nucleotide sequence was compared with the nucleotide sequences of other fluorescent protein genes, so as to determine whether the nucleotide sequence of the DNA fragment was derived from a fluorescent protein. With regard to those that were determined to be a part of the fluorescent protein genes, the full-length genes were cloned by the 5'-RACE method and the 3'-RACE method.

(5) 5'-RACE Method

In order to determine the nucleotide sequence on the 5'-side of the DNA fragment obtained by the degenerated PCR, the 5'-RACE method was applied using 5'-RACE System for Rapid Amplification of cDNA Ends, Version 2.0 (GIBCO BRL). 3 μg of the total RNA prepared in (1) above was used as a template.

The following primers were used in the first amplification of dC-tailed cDNA:

```
                                          (SEQ ID NO: 17)
5'-GGCCACGCGTCGACTAGTACGGGIIGGGIIGGGIIG-3'
(Primer 4);
and (SEQ ID NO: 41)
5'-TTG TCA AGA TAT CGA AAG CGA ACG GCA GAG-3'
(Primer 5).
```

Herein, I represents inosine.

The following primers were used in the second amplification:

```
                                          (SEQ ID NO: 42)
5'-GGCCACGCGTCGACTAGTAC-3' (Primer 6);
and (SEQ ID NO: 43)
5'-CTT CTC ACG TTG CAA ATG GC-3' (Primer 7).
```

PCR reaction conditions were applied in accordance with protocols attached to the kit.

The amplified 600-bp band was cut out of the gel via agarose gel electrophoresis and then purified. The purified DNA fragment was ligated to a pT7-blue vector (Novagen). Escherichia coli (TG1) was transformed therewith, and it was then subjected to blue white selection. Plasmid DNA was purified from white colonies of Escherichia coli, and the nucleotide sequence of the inserted DNA fragment was determined using a DNA sequencer.

(6) Determination of Full Length Nucleotide Sequence, and Expression of Protein in Escherichia coli A primer was produced with a portion corresponding to the N-terminus of the protein obtained in (5) above. An oligo dT primer was used as a primer corresponding to the C-terminal side thereof. Thereafter, using such primers, PCR was carried out employing the first strand cDNA prepared in (2) above as a template.

Primer used:

```
                                          (SEQ ID NO: 44)
5'-CCC GGA TCC GAT GAG TGT GAT TAC AWC AGA AAT GAA
GAT GGA GC-3' (Primer 8)
```

Composition of PCR reaction solution:

| | |
|---|---|
| Template (first strand cDNA) | 3 μl |
| X10 TAQ (polymerase) buffer | 5 μl |
| 2.5 mM dNTPs | 4 μl |
| 100 μM primer 8 | 1 μl |
| 100 μM oligo dT primer | 1 μl |
| MILLI-Q (reagent grade water) | 35 μl |
| PYROBEST polymerase (5 U/μl) | 1 μl |

PCR reaction conditions:
94° C. ×1 minute (PAD)
94° C. ×30 seconds (denaturation)
52° C. ×30 seconds (annealing of primers to template)
72° C. ×1 minute (primer elongation)
4° C. (maintenance)

The amplified band with a length of approximately 900 bp was cut out of the gel via agarose gel electrophoresis and then purified. The purified DNA fragment was subcloned into the BamHI-EcoRI site of a pRSET vector (Invitrogen), and it was then allowed to express in Escherichia coli (JM109-DE3). In addition, the plasmid was recovered, and the full length nucleotide sequence that had been inserted was determined. The clone was named KnG. The full length nucleotide sequence thereof and the full length amino acid sequence thereof are shown in SEQ ID NOS: 14 and 13 of the sequence listing, respectively.

The expressed protein was constructed such that His-tag was attached to the N-terminus thereof, and thus it was purified with Ni-Agarose gel (QIAGEN). Purification was carried out in accordance with the attached protocols. Subsequently, the properties of the purified protein were analyzed.

(7) Analysis of Fluorescence Properties

Figure 8:
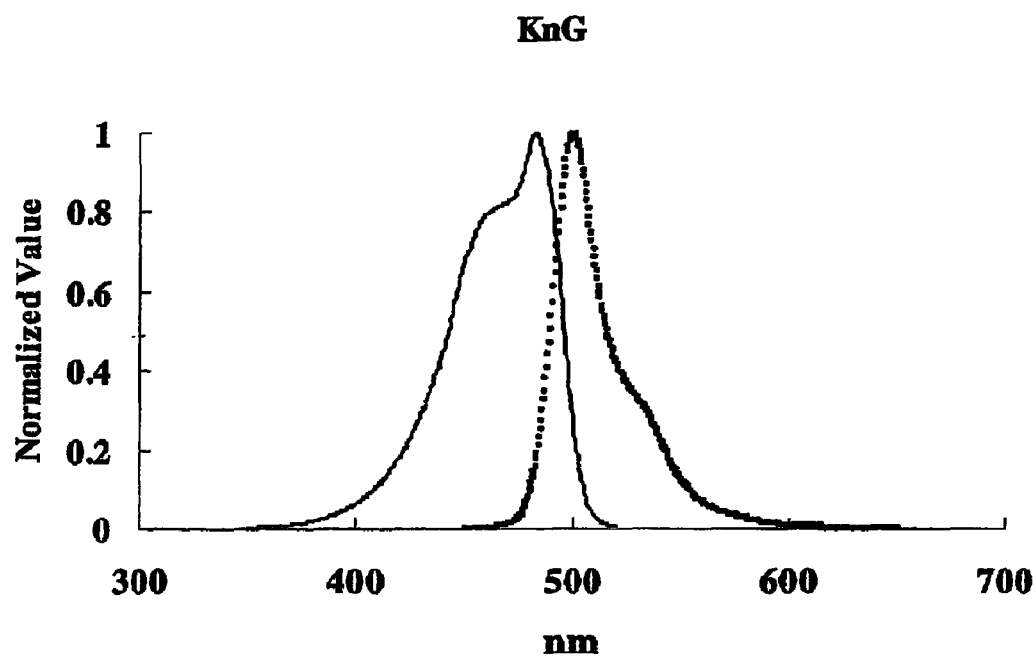
FIG. 8 shows the fluorescence spectrum and excitation spectrum of the fluorescent protein (KnG) of the present invention derived from *Lobophytum crassum* (FIG. A), and the pH dependence of the fluorescent protein (KnG) (FIG. B).
Figure 8:
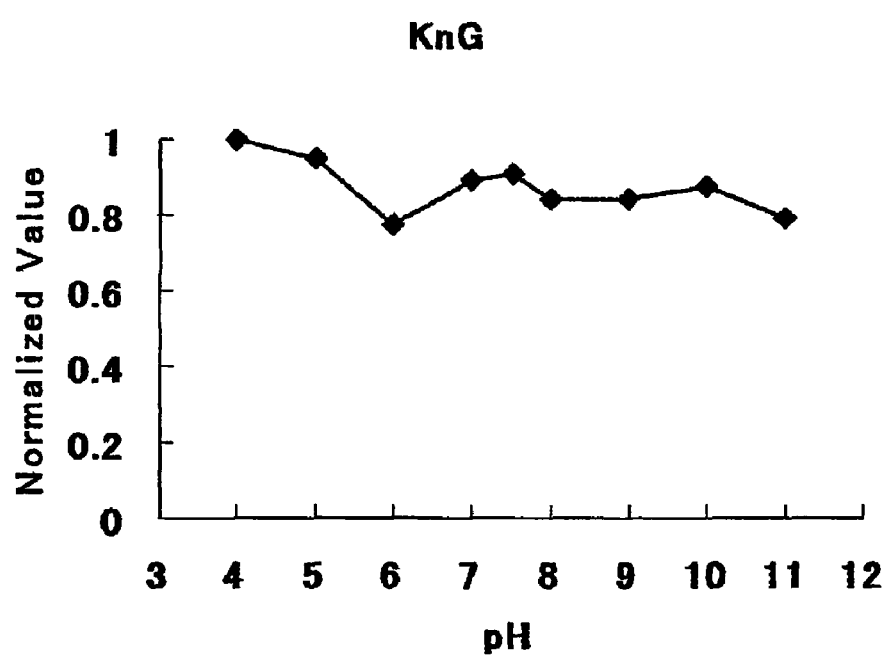

Using a solution comprising 10 μM fluorescent protein (KnG) and 50 mM HEPES (pH 7.9), the absorption spectrum of the protein was measured (FIG. 8A). Thereafter, the molar absorption coefficient of the protein was calculated from the peak value of the spectrum. The absorption peak was observed at 482 nm. The fluorescent protein was diluted with the above buffer solution such that the absorption at 450 nm became 0.005. The fluorescence spectrum obtained by excitation at 450 m was measured (FIG. 8A). Likewise, EGFP (CLONTECH) was diluted such that the absorption at 450 nm became 0.005, and the fluorescence spectrum was measured. Setting the quantum yield of EGFP to 0.6, the quantum yield of the novel protein was obtained. The results are shown in Table 6.

TABLE 6

| | Excitation maximum | Fluorescence maximum | Molar absorption coefficient | Quantum yield | pH sensitivity | Number of amino acids |
|---|---|---|---|---|---|---|
| KnG | 482 nm | 498 nm | 71,000 (482 nm) | 0.41 | Stable between pH 4 and pH 10 | 224 |

(8) Measurement of pH Sensitivity

The fluorescent protein was diluted with each of the following buffer solutions. Thereafter, the fluorescence spectrum was measured. The pH levels of the buffer solutions are as follows.

pH 4 and 5: Acetate buffer
pH 6: MES buffer
pH 7: MOPS buffer
pH 8: HEPES buffer
pH 9 and 10: Glycine buffer
pH 11: Phosphate buffer The results are shown in FIG. 8B.

INDUSTRIAL APPLICABILITY

The present invention provides novel fluorescent proteins derived from Montipora sp., Acropora sp., and Lobophytum crassum. The fluorescent proteins of the present invention are novel proteins having a primary structure different from that of the conventional fluorescent proteins. The fluorescent proteins of the present invention have certain fluorescence properties, and thus they are useful for molecular biological analysis. That is to say, the use of fluorescent proteins of the present invention enables fluorescent labeling in mammalian cells without exhibiting toxicity. In addition, a mutation is introduced into the fluorescent proteins of the present invention, so as to generate new fluorescence properties.

Moreover, when compared with the wide excitation spectrum of the conventional RFP (DsRed; CLONTECH), the fluorescent protein (COR) of the present invention has a sharper spectrum. Furthermore, a mutation is introduced into the fluorescent protein of the present invention, so as to diversify the fluorescence properties in the red region.

Still further, the present invention provides a novel chromoprotein derived from Actinia equina. Since the chromoprotein of the present invention exhibits absorption in the red region and its pH sensitivity thereof is low, it is useful for molecular biological analysis. Still further, since the absorption degree (molar absorption coefficient) of the chromoprotein of the present invention is significantly large, it makes possible to efficiently convert light energy to other types of energy. It is also possible to bring the quantum yield of the chromoprotein of the present invention to close to 1 by genetic modification technology. In such a case, a novel fluorescent protein can be produced.

The invention claimed is:

1. An isolated DNA encoding a fluorescent protein comprising the amino acid sequence shown in SEQ ID NO: 5.

2. An isolated DNA comprising the nucleotide sequence shown in SEQ ID NO: 6, which encodes a fluorescent protein.

3. An isolated DNA encoding a fluorescent protein comprising the amino acid sequence shown in SEQ ID NO: 7.

4. An isolated DNA comprising the nucleotide sequence shown in SEQ ID NO: 8, which encodes a fluorescent protein.

* * * * *

SEQUENCE LISTING

```
<160> NUMBER OF SEQ ID NOS: 44

<210> SEQ ID NO 1
<211> LENGTH: 227
<212> TYPE: PRT
<213> ORGANISM: Montipora sp.

<400> SEQUENCE: 1

Met Ala Leu Ser Lys Arg Gly Val Lys Gly Glu Met Lys Leu Lys Phe
 1               5                   10                  15

His Met Glu Gly Cys Val Asn Gly His Glu Phe Thr Ile Lys Gly Glu
             20                  25                  30
```

```
Gly Thr Gly Gln Pro Tyr Glu Gly Thr Gln Cys Ile Gln Leu Arg Val
         35                  40                  45

Glu Lys Gly Gly Pro Leu Pro Phe Ser Val Asp Ile Leu Ser Ala Ala
 50                  55                  60

Phe Leu Tyr Gly Asn Arg Cys Met Thr Lys Tyr Pro Gly Gly Ile Val
 65                  70                  75                  80

Asp Tyr Phe Lys Asn Ser Cys Pro Ala Gly Tyr Thr Trp Glu Arg Ser
                 85                  90                  95

Phe Leu Phe Glu Asp Gly Ala Val Cys Thr Ala Ser Ala Asp Ile Arg
            100                 105                 110

Leu Ser Val Glu Asp Asn Cys Phe Tyr His Glu Ser Lys Phe Ser Gly
        115                 120                 125

Val Asn Phe Pro Val Asp Gly Pro Val Met Thr Leu Ala Thr Thr Gly
    130                 135                 140

Trp Glu Pro Ser Ser Glu Lys Met Val Pro Ser Gly Gly Ile Val Lys
145                 150                 155                 160

Gly Asp Val Thr Met Tyr Leu Leu Leu Lys Asp Gly Arg Tyr Arg
                165                 170                 175

Cys Gln Phe Asn Ser Asn Tyr Lys Ala Lys Thr Glu Pro Lys Glu Met
                180                 185                 190

Pro Asp Phe His Phe Val Glu His Lys Ile Val Arg Thr Asp Leu Gly
            195                 200                 205

Gly Arg Asp Gln Lys Trp Gln Leu Val Gly Asn Ser Ala Ala Cys Ala
210                 215                 220

Ser Ala Phe
225

<210> SEQ ID NO 2
<211> LENGTH: 684
<212> TYPE: DNA
<213> ORGANISM: Montipora sp.
<220> FEATURE:
<221> NAME/KEY: CDS
<222> LOCATION: (1)..(681)

<400> SEQUENCE: 2 atg gct ctt tca aag cga ggt gtc aaa ggc gaa atg aaa ctg aaa ttc      48
Met Ala Leu Ser Lys Arg Gly Val Lys Gly Glu Met Lys Leu Lys Phe
 1               5                  10                  15 cat atg gag ggg tgt gtt aac ggg cat gaa ttt aca atc aag ggc gaa      96
His Met Glu Gly Cys Val Asn Gly His Glu Phe Thr Ile Lys Gly Glu
             20                  25                  30 ggc act ggg caa cct tac gaa ggg aca cag tgt att caa ctc cgt gtg     144
Gly Thr Gly Gln Pro Tyr Glu Gly Thr Gln Cys Ile Gln Leu Arg Val
         35                  40                  45 gaa aaa ggg ggt cca ttg cca ttc tca gta gac ata ttg tcg gct gcg     192
Glu Lys Gly Gly Pro Leu Pro Phe Ser Val Asp Ile Leu Ser Ala Ala
 50                  55                  60 ttt cta tac gga aac agg tgc atg acc aaa tat cct gga ggc ata gtt     240
Phe Leu Tyr Gly Asn Arg Cys Met Thr Lys Tyr Pro Gly Gly Ile Val
 65                  70                  75                  80 gac tat ttc aag aac tca tgc cct gct gga tat aca tgg gaa agg tct     288
Asp Tyr Phe Lys Asn Ser Cys Pro Ala Gly Tyr Thr Trp Glu Arg Ser
                 85                  90                  95 ttt ctc ttt gaa gat ggc gcg gtg tgc aca gca agt gca gat ata cgc     336
Phe Leu Phe Glu Asp Gly Ala Val Cys Thr Ala Ser Ala Asp Ile Arg
            100                 105                 110 ttg agt gtc gag gat aac tgc ttt tat cac gaa tcc aag ttt agt gga     384
Leu Ser Val Glu Asp Asn Cys Phe Tyr His Glu Ser Lys Phe Ser Gly
```

```
                 115                 120                 125
gta aac ttt cct gtt gat gga cct gtg atg aca ctg gcg acg act ggt    432
Val Asn Phe Pro Val Asp Gly Pro Val Met Thr Leu Ala Thr Thr Gly
    130                 135                 140 tgg gag cca tcc tcc gag aaa atg gtg ccc agt ggg ggg ata gtg aaa    480
Trp Glu Pro Ser Ser Glu Lys Met Val Pro Ser Gly Gly Ile Val Lys
145                 150                 155                 160 ggg gat gtc acc atg tac ctc ctt ctg aag gat ggt ggg cgt tac cgg    528
Gly Asp Val Thr Met Tyr Leu Leu Leu Lys Asp Gly Gly Arg Tyr Arg
                165                 170                 175 tgc cag ttc aac agt aat tac aag gca aag act gag ccg aaa gag atg    576
Cys Gln Phe Asn Ser Asn Tyr Lys Ala Lys Thr Glu Pro Lys Glu Met
            180                 185                 190 cca gac ttt cac ttc gtg gag cat aag atc gta agg acc gac ctc ggt    624
Pro Asp Phe His Phe Val Glu His Lys Ile Val Arg Thr Asp Leu Gly
        195                 200                 205 ggc cga gac cag aaa tgg caa ctg gtg gga aat tct gct gca tgt gca    672
Gly Arg Asp Gln Lys Trp Gln Leu Val Gly Asn Ser Ala Ala Cys Ala
    210                 215                 220 agc gct ttc taa                                                    684
Ser Ala Phe
225

<210> SEQ ID NO 3
<211> LENGTH: 232
<212> TYPE: PRT
<213> ORGANISM: Acropora sp.

<400> SEQUENCE: 3

Met Val Ser Tyr Ser Lys Gln Gly Ile Ala Gln Glu Met Lys Thr Lys
1               5                   10                  15

Tyr His Met Glu Gly Ser Val Asn Gly His Glu Phe Thr Ile Glu Gly
            20                  25                  30

Val Ala Thr Gly Tyr Pro Tyr Glu Gly Lys Gln Met Ser Glu Leu Val
        35                  40                  45

Ile Ile Lys Pro Ala Gly Lys Pro Leu Pro Phe Ser Phe Asp Ile Leu
    50                  55                  60

Ser Ser Val Phe His Tyr Gly Asn Arg Cys Phe Thr Lys Tyr Pro Ala
65                  70                  75                  80

Asp Met Pro Asp Tyr Phe Lys Gln Ala Phe Pro Asp Gly Met Ser Tyr
                85                  90                  95

Glu Arg Ser Phe Leu Phe Glu Asp Gly Ala Val Ala Thr Ala Ser Trp
            100                 105                 110

Asn Ile Arg Leu Glu Gly Asn Cys Phe Ile His Asn Ser Ile Phe His
        115                 120                 125

Gly Val Asn Phe Pro Ala Asp Gly Pro Val Met Lys Lys Gln Thr Ile
    130                 135                 140

Asp Trp Glu Lys Ser Phe Glu Lys Met Thr Val Ser Lys Glu Val Leu
145                 150                 155                 160

Arg Gly Asp Val Thr Met Phe Leu Met Leu Glu Gly Gly Ser His
                165                 170                 175

Arg Cys Gln Phe His Ser Thr Tyr Lys Thr Glu Lys Pro Val Ala Met
            180                 185                 190

Pro Pro Asn His Val Val Glu His Gln Ile Val Arg Thr Asp Leu Gly
        195                 200                 205

Gln Ser Ala Lys Gly Phe Thr Val Lys Leu Glu Ala His Ala Val Ala
    210                 215                 220
```

```
His Val Asn Pro Leu Lys Val Lys
225                 230

<210> SEQ ID NO 4
<211> LENGTH: 699
<212> TYPE: DNA
<213> ORGANISM: Acropora sp.
<220> FEATURE:
<221> NAME/KEY: CDS
<222> LOCATION: (1)..(696)

<400> SEQUENCE: 4 atg gtg tct tat tca aag caa ggc atc gca caa gaa atg aag acg aaa       48
Met Val Ser Tyr Ser Lys Gln Gly Ile Ala Gln Glu Met Lys Thr Lys
 1               5                  10                  15 tac cat atg gaa ggc agt gtc aat ggc cat gaa ttc acg atc gaa ggt       96
Tyr His Met Glu Gly Ser Val Asn Gly His Glu Phe Thr Ile Glu Gly
             20                  25                  30 gta gca act ggg tac cct tac gaa ggg aaa cag atg tcc gaa tta gtg      144
Val Ala Thr Gly Tyr Pro Tyr Glu Gly Lys Gln Met Ser Glu Leu Val
         35                  40                  45 atc atc aag cct gcg gga aaa ccc ctt cca ttc tcc ttt gac ata ctg      192
Ile Ile Lys Pro Ala Gly Lys Pro Leu Pro Phe Ser Phe Asp Ile Leu
     50                  55                  60 tca tca gtc ttt cat tat gga aac agg tgc ttc aca aag tac cct gca      240
Ser Ser Val Phe His Tyr Gly Asn Arg Cys Phe Thr Lys Tyr Pro Ala
 65                  70                  75                  80 gac atg cct gac tat ttc aag caa gca ttc cca gat gga atg tcg tat      288
Asp Met Pro Asp Tyr Phe Lys Gln Ala Phe Pro Asp Gly Met Ser Tyr
                 85                  90                  95 gaa agg tca ttt cta ttt gaa gat gga gca gtt gct aca gcc agc tgg      336
Glu Arg Ser Phe Leu Phe Glu Asp Gly Ala Val Ala Thr Ala Ser Trp
            100                 105                 110 aac att cgt ctc gaa gga aat tgc ttc atc cac aat tcc atc ttt cat      384
Asn Ile Arg Leu Glu Gly Asn Cys Phe Ile His Asn Ser Ile Phe His
        115                 120                 125 ggc gta aac ttt ccc gct gat gga ccc gta atg aaa aag cag aca att      432
Gly Val Asn Phe Pro Ala Asp Gly Pro Val Met Lys Lys Gln Thr Ile
    130                 135                 140 gac tgg gag aag tcc ttc gaa aaa atg act gtg tct aaa gag gtg cta      480
Asp Trp Glu Lys Ser Phe Glu Lys Met Thr Val Ser Lys Glu Val Leu
145                 150                 155                 160 aga ggt gat gtg act atg ttt ctt atg ctc gaa gga ggt ggt tct cac      528
Arg Gly Asp Val Thr Met Phe Leu Met Leu Glu Gly Gly Gly Ser His
                165                 170                 175 aga tgc cag ttt cac tcc act tac aaa aca gag aag ccg gtc gca atg      576
Arg Cys Gln Phe His Ser Thr Tyr Lys Thr Glu Lys Pro Val Ala Met
            180                 185                 190 ccc ccg aat cat gtc gta gaa cat caa att gtg agg acc gac ctt ggc      624
Pro Pro Asn His Val Val Glu His Gln Ile Val Arg Thr Asp Leu Gly
        195                 200                 205 caa agt gca aaa ggc ttt aca gtc aag ctg gaa gca cat gct gtg gct      672
Gln Ser Ala Lys Gly Phe Thr Val Lys Leu Glu Ala His Ala Val Ala
    210                 215                 220 cat gtt aac cct ttg aag gtt aaa taa                                  699
His Val Asn Pro Leu Lys Val Lys
225                 230

<210> SEQ ID NO 5
<211> LENGTH: 232
<212> TYPE: PRT
<213> ORGANISM: Acropora sp.
```

-continued

<400> SEQUENCE: 5

```
Met Val Ser Tyr Ser Lys Gln Gly Ile Ala Gln Glu Met Arg Thr Lys
1               5                   10                  15

Tyr Arg Met Glu Gly Ser Val Asn Gly His Glu Phe Thr Ile Glu Gly
            20                  25                  30

Val Gly Thr Gly Asn Pro Tyr Glu Gly Lys Gln Met Ser Glu Leu Val
        35                  40                  45

Ile Ile Lys Ser Lys Gly Lys Pro Leu Pro Phe Ser Phe Asp Ile Leu
    50                  55                  60

Ser Thr Ala Phe Gln Tyr Gly Asn Arg Cys Phe Thr Lys Tyr Pro Ala
65                  70                  75                  80

Asp Met Pro Asp Tyr Phe Lys Gln Ala Phe Pro Asp Gly Met Ser Tyr
                85                  90                  95

Glu Arg Ser Phe Leu Phe Glu Asp Gly Val Ala Thr Ala Ser Trp
            100                 105                 110

Ser Ile Arg Leu Glu Gly Asn Cys Phe Ile His Asn Ser Ile Tyr His
        115                 120                 125

Gly Val Asn Phe Pro Ala Asp Gly Pro Val Met Lys Lys Gln Thr Ile
    130                 135                 140

Gly Trp Asp Lys Ser Phe Glu Lys Met Ser Val Ala Lys Glu Val Leu
145                 150                 155                 160

Arg Gly Asp Val Thr Gln Phe Leu Leu Leu Glu Gly Gly Tyr Gln
                165                 170                 175

Arg Cys Arg Phe His Ser Thr Tyr Lys Thr Glu Lys Pro Val Ala Met
            180                 185                 190

Pro Pro Ser His Val Val Glu His Gln Ile Val Arg Thr Asp Leu Gly
        195                 200                 205

Gln Thr Ala Lys Gly Phe Lys Val Lys Leu Glu Glu His Ala Glu Ala
    210                 215                 220

His Val Asn Pro Leu Lys Val Lys
225                 230
```

<210> SEQ ID NO 6
<211> LENGTH: 699
<212> TYPE: DNA
<213> ORGANISM: Acropora sp.
<220> FEATURE:
<221> NAME/KEY: CDS
<222> LOCATION: (1)..(696)

<400> SEQUENCE: 6

```
atg gtg tct tat tca aag caa ggc atc gca caa gaa atg cgg acg aaa      48
Met Val Ser Tyr Ser Lys Gln Gly Ile Ala Gln Glu Met Arg Thr Lys
1               5                   10                  15 tac cgt atg gaa ggc agt gtc aat ggc cat gaa ttc acg atc gaa ggt      96
Tyr Arg Met Glu Gly Ser Val Asn Gly His Glu Phe Thr Ile Glu Gly
            20                  25                  30 gta gga act gga aac cct tac gaa ggg aaa cag atg tcc gaa tta gtg     144
Val Gly Thr Gly Asn Pro Tyr Glu Gly Lys Gln Met Ser Glu Leu Val
        35                  40                  45 atc atc aag tct aag gga aaa ccc ctt cca ttc tcc ttt gac ata ctg     192
Ile Ile Lys Ser Lys Gly Lys Pro Leu Pro Phe Ser Phe Asp Ile Leu
    50                  55                  60 tca aca gcc ttt caa tat gga aac aga tgc ttc aca aag tac cct gca     240
Ser Thr Ala Phe Gln Tyr Gly Asn Arg Cys Phe Thr Lys Tyr Pro Ala
65                  70                  75                  80 gac atg cct gac tat ttc aag caa gca ttc cca gat gga atg tca tat     288
Asp Met Pro Asp Tyr Phe Lys Gln Ala Phe Pro Asp Gly Met Ser Tyr
```

```
                        85                  90                  95
gaa agg tca ttt cta ttt gag gat gga gga gtt gct aca gcc agc tgg      336
Glu Arg Ser Phe Leu Phe Glu Asp Gly Gly Val Ala Thr Ala Ser Trp
            100                 105                 110 agc att cgt ctc gaa gga aat tgc ttc atc cac aat tcc atc tat cat      384
Ser Ile Arg Leu Glu Gly Asn Cys Phe Ile His Asn Ser Ile Tyr His
            115                 120                 125 ggc gta aac ttt ccc gct gat gga ccc gta atg aag aag cag aca att      432
Gly Val Asn Phe Pro Ala Asp Gly Pro Val Met Lys Lys Gln Thr Ile
        130                 135                 140 ggc tgg gat aag tcc ttc gaa aaa atg agt gtg gct aaa gag gtg cta      480
Gly Trp Asp Lys Ser Phe Glu Lys Met Ser Val Ala Lys Glu Val Leu
145                 150                 155                 160 aga ggt gat gtg act cag ttt ctt ctg ctc gaa gga ggt ggt tac cag      528
Arg Gly Asp Val Thr Gln Phe Leu Leu Leu Glu Gly Gly Gly Tyr Gln
                165                 170                 175 aga tgc cgg ttt cac tcc act tac aaa acg gag aag cca gtc gca atg      576
Arg Cys Arg Phe His Ser Thr Tyr Lys Thr Glu Lys Pro Val Ala Met
            180                 185                 190 ccc ccg agt cat gtc gta gaa cat caa att gtg agg acc gac ctt ggc      624
Pro Pro Ser His Val Val Glu His Gln Ile Val Arg Thr Asp Leu Gly
        195                 200                 205 caa act gca aaa ggc ttc aag gtc aag ctg gaa gaa cat gct gag gct      672
Gln Thr Ala Lys Gly Phe Lys Val Lys Leu Glu Glu His Ala Glu Ala
210                 215                 220 cat gtt aac cct ttg aag gtt aaa taa                                  699
His Val Asn Pro Leu Lys Val Lys
225                 230

<210> SEQ ID NO 7
<211> LENGTH: 232
<212> TYPE: PRT
<213> ORGANISM: Acropora sp.

<400> SEQUENCE: 7

Met Val Ser Tyr Ser Lys Gln Gly Ile Ala Gln Glu Met Arg Thr Lys
1               5                   10                  15

Tyr Arg Met Glu Gly Ser Val Asn Gly His Glu Phe Thr Ile Glu Gly
            20                  25                  30

Val Gly Thr Gly Asn Pro Tyr Glu Gly Lys Gln Met Ser Glu Leu Val
        35                  40                  45

Ile Ile Lys Ser Lys Gly Lys Pro Leu Pro Phe Ser Phe Asp Ile Leu
    50                  55                  60

Ser Thr Ala Phe Gln Tyr Gly Asn Arg Cys Phe Thr Lys Tyr Pro Ala
65                  70                  75                  80

Asp Met Pro Asp Tyr Phe Lys Gln Ala Phe Pro Asp Gly Met Ser Tyr
                85                  90                  95

Glu Arg Ser Phe Leu Phe Glu Asp Gly Gly Val Ala Thr Ala Ser Trp
            100                 105                 110

Ser Ile Arg Leu Glu Gly Asn Cys Phe Ile His Asn Ser Ile Tyr His
        115                 120                 125

Gly Val Asn Phe Pro Ala Asp Gly Pro Val Met Lys Lys Gln Thr Ile
    130                 135                 140

Gly Trp Asp Lys Ser Phe Glu Lys Met Ser Val Ala Lys Glu Val Leu
145                 150                 155                 160

Arg Gly Asp Val Thr His Phe Leu Leu Leu Glu Gly Gly Gly Tyr Gln
                165                 170                 175

Arg Cys Arg Phe His Ser Thr Tyr Lys Thr Glu Lys Pro Val Ala Met
```

```
                    180                 185                 190
Pro Pro Ser His Val Val Glu His Gln Ile Val Arg Thr Asp Leu Gly
        195                 200                 205

Gln Thr Ala Lys Gly Phe Lys Val Lys Leu Glu Glu His Ala Glu Ala
    210                 215                 220

His Val Asn Pro Leu Lys Val Lys
225                 230

<210> SEQ ID NO 8
<211> LENGTH: 699
<212> TYPE: DNA
<213> ORGANISM: Acropora sp.
<220> FEATURE:
<221> NAME/KEY: CDS
<222> LOCATION: (1)..(696)

<400> SEQUENCE: 8 atg gtg tct tat tca aag caa ggc atc gca caa gaa atg cgg acg aaa      48
Met Val Ser Tyr Ser Lys Gln Gly Ile Ala Gln Glu Met Arg Thr Lys
  1               5                  10                  15 tac cgt atg gaa ggc agt gtc aat ggc cat gaa ttc acg atc gaa ggt      96
Tyr Arg Met Glu Gly Ser Val Asn Gly His Glu Phe Thr Ile Glu Gly
                 20                  25                  30 gta gga act gga aac cct tac gaa ggg aaa cag atg tcc gaa tta gtg     144
Val Gly Thr Gly Asn Pro Tyr Glu Gly Lys Gln Met Ser Glu Leu Val
             35                  40                  45 atc atc aag tct aag gga aaa ccc ctt cca ttc tcc ttt gac ata ctg     192
Ile Ile Lys Ser Lys Gly Lys Pro Leu Pro Phe Ser Phe Asp Ile Leu
         50                  55                  60 tca aca gcc ttt caa tat gga aac aga tgc ttc aca aag tac cct gca     240
Ser Thr Ala Phe Gln Tyr Gly Asn Arg Cys Phe Thr Lys Tyr Pro Ala
 65                  70                  75                  80 gac atg cct gac tat ttc aag caa gca ttc cca gat gga atg tca tat     288
Asp Met Pro Asp Tyr Phe Lys Gln Ala Phe Pro Asp Gly Met Ser Tyr
                 85                  90                  95 gaa agg tca ttt cta ttt gag gat gga gga gtt gct aca gcc agc tgg     336
Glu Arg Ser Phe Leu Phe Glu Asp Gly Gly Val Ala Thr Ala Ser Trp
            100                 105                 110 agc att cgt ctc gaa gga aat tgc ttc atc cac aat tcc atc tat cat     384
Ser Ile Arg Leu Glu Gly Asn Cys Phe Ile His Asn Ser Ile Tyr His
        115                 120                 125 ggc gta aac ttt ccc gct gat gga ccc gta atg aag aag cag aca att     432
Gly Val Asn Phe Pro Ala Asp Gly Pro Val Met Lys Lys Gln Thr Ile
    130                 135                 140 ggc tgg gat aag tcc ttc gaa aaa atg agt gtg gct aaa gag gtg cta     480
Gly Trp Asp Lys Ser Phe Glu Lys Met Ser Val Ala Lys Glu Val Leu
145                 150                 155                 160 aga ggt gat gtg act cat ttt ctt ctg ctc gaa gga ggt ggt tac cag     528
Arg Gly Asp Val Thr His Phe Leu Leu Leu Glu Gly Gly Gly Tyr Gln
                165                 170                 175 aga tgc cgg ttt cac tcc act tac aaa acg gag aag cca gtc gca atg     576
Arg Cys Arg Phe His Ser Thr Tyr Lys Thr Glu Lys Pro Val Ala Met
            180                 185                 190 ccc ccg agt cat gtc gta gaa cat caa att gtg agg acc gac ctt ggc     624
Pro Pro Ser His Val Val Glu His Gln Ile Val Arg Thr Asp Leu Gly
        195                 200                 205 caa act gca aaa ggc ttc aag gtc aag ctg gaa gaa cat gct gag gct     672
Gln Thr Ala Lys Gly Phe Lys Val Lys Leu Glu Glu His Ala Glu Ala
    210                 215                 220 cat gtt aac cct ttg aag gtt aaa taa                                 699
His Val Asn Pro Leu Lys Val Lys
```

```
<210> SEQ ID NO 9
<211> LENGTH: 232
<212> TYPE: PRT
<213> ORGANISM: Montipora sp.

<400> SEQUENCE: 9

Met Ala Leu Ser Lys His Gly Leu Thr Lys Asn Met Thr Thr Lys Tyr
 1               5                  10                  15

Arg Met Glu Gly Cys Val Asp Gly His Lys Phe Val Ile Thr Gly Asp
                20                  25                  30

Gly Ile Gly Asp Pro Phe Glu Gly Lys Gln Thr Ser Ile Asp Leu Cys
            35                  40                  45

Val Val Glu Gly Gly Pro Leu Pro Phe Ser Glu Asp Ile Leu Ser Ala
 50                  55                  60

Val Phe Asp Tyr Gly Asn Arg Val Phe Thr Lys Tyr Pro Gln Asp Leu
 65                  70                  75                  80

Val Asp Tyr Phe Lys Asn Ser Cys Pro Ala Gly Tyr Thr Trp Gln Arg
                85                  90                  95

Ser Phe Leu Phe Glu Asp Gly Ala Val Cys Thr Ala Ser Ala Asp Ile
               100                 105                 110

Arg Val Ser Val Glu Glu Asn Cys Phe Tyr His Glu Ser Lys Phe His
           115                 120                 125

Gly Val Asn Phe Pro Ala Asp Gly Pro Val Met Lys Lys Met Thr Thr
130                 135                 140

Asn Trp Glu Pro Ser Cys Glu Lys Ile Thr Pro Ile Leu Asn Glu Gly
145                 150                 155                 160

Ile Leu Lys Gly Asp Val Thr Met Phe Leu Leu Leu Lys Asp Gly Gly
                165                 170                 175

Arg Tyr Arg Cys Gln Phe Asp Thr Val Tyr Lys Ala Lys Ala Asp Ala
            180                 185                 190

Lys Lys Met Pro Glu Trp His Phe Ile Gln His Lys Leu Thr Arg Glu
        195                 200                 205

Asp Arg Ser Asp Ala Lys His Gln Lys Trp Arg Leu Val Glu Asn Ala
210                 215                 220

Ile Ala Tyr Arg Ser Thr Leu Pro
225                 230

<210> SEQ ID NO 10
<211> LENGTH: 699
<212> TYPE: DNA
<213> ORGANISM: Montipora sp.
<220> FEATURE:
<221> NAME/KEY: CDS
<222> LOCATION: (1)..(696)

<400> SEQUENCE: 10 atg gct ctt tca aag cac ggt cta aca aag aac atg acg acg aaa tac    48
Met Ala Leu Ser Lys His Gly Leu Thr Lys Asn Met Thr Thr Lys Tyr
 1               5                  10                  15 cgc atg gaa ggg tgt gtc gat ggg cat aaa ttt gta atc acg ggc gac    96
Arg Met Glu Gly Cys Val Asp Gly His Lys Phe Val Ile Thr Gly Asp
                20                  25                  30 ggc att gga gat cct ttc gaa ggg aaa cag act agt att gat ctg tgt   144
Gly Ile Gly Asp Pro Phe Glu Gly Lys Gln Thr Ser Ile Asp Leu Cys
            35                  40                  45 gtg gtt gaa ggg gga cca ctg cca ttc tcc gaa gat ata ttg tct gct   192
Val Val Glu Gly Gly Pro Leu Pro Phe Ser Glu Asp Ile Leu Ser Ala
```

```
                  50                      55                      60
gtg ttt gac tac gga aac agg gtc ttt act aaa tat cct caa gac ctt         240
Val Phe Asp Tyr Gly Asn Arg Val Phe Thr Lys Tyr Pro Gln Asp Leu
 65                      70                      75                  80 gtt gac tat ttc aag aac tca tgt cct gct gga tat aca tgg caa agg         288
Val Asp Tyr Phe Lys Asn Ser Cys Pro Ala Gly Tyr Thr Trp Gln Arg
                         85                      90                  95 tct ttt ctc ttt gaa gat ggt gca gtt tgc aca gcc agt gca gat ata         336
Ser Phe Leu Phe Glu Asp Gly Ala Val Cys Thr Ala Ser Ala Asp Ile
                100                     105                     110 aga gtg agt gtt gag gag aac tgc ttt tat cac gag tcc aag ttt cat         384
Arg Val Ser Val Glu Glu Asn Cys Phe Tyr His Glu Ser Lys Phe His
            115                     120                     125 gga gtg aac ttt cct gct gat gga cct gtg atg aaa aag atg aca act         432
Gly Val Asn Phe Pro Ala Asp Gly Pro Val Met Lys Lys Met Thr Thr
130                     135                     140 aat tgg gaa cca tcc tgc gag aaa atc aca cca ata ctt aat gag ggg         480
Asn Trp Glu Pro Ser Cys Glu Lys Ile Thr Pro Ile Leu Asn Glu Gly
145                     150                     155                 160 ata ttg aaa gga gat gtc acc atg ttc ctc ctt ctg aag gat ggt ggg         528
Ile Leu Lys Gly Asp Val Thr Met Phe Leu Leu Leu Lys Asp Gly Gly
                165                     170                     175 cgt tac cgg tgc cag ttc gac aca gtt tac aaa gca aag gct gac gca         576
Arg Tyr Arg Cys Gln Phe Asp Thr Val Tyr Lys Ala Lys Ala Asp Ala
                180                     185                     190 aaa aag atg ccg gaa tgg cac ttc atc caa cat aag ctc acc cgg gaa         624
Lys Lys Met Pro Glu Trp His Phe Ile Gln His Lys Leu Thr Arg Glu
            195                     200                     205 gac cgc agc gat gct aag cac cag aaa tgg cga ctg gta gaa aat gct         672
Asp Arg Ser Asp Ala Lys His Gln Lys Trp Arg Leu Val Glu Asn Ala
210                     215                     220 att gca tac cga tcc aca tta ccc tga                                     699
Ile Ala Tyr Arg Ser Thr Leu Pro
225                 230

<210> SEQ ID NO 11
<211> LENGTH: 232
<212> TYPE: PRT
<213> ORGANISM: Actinia equina

<400> SEQUENCE: 11

Met Ser Ser Leu Val Lys Lys Asp Met Cys Ile Lys Met Thr Met Glu
  1               5                  10                  15

Gly Thr Val Asn Gly His His Phe Lys Cys Val Gly Glu Gly Glu Gly
                 20                  25                  30

Lys Pro Phe Glu Gly Thr Gln Glu Glu Lys Ile Arg Ile Thr Glu Gly
             35                  40                  45

Gly Pro Leu Pro Phe Ala Tyr Asp Ile Leu Ala Pro Cys Cys Met Tyr
         50                  55                  60

Gly Ser Lys Thr Phe Ile Lys His Val Ser Gly Ile Pro Asp Tyr Phe
 65                  70                  75                  80

Lys Asp Ser Leu Pro Glu Gly Tyr Thr Trp Glu Arg Thr Gln Ile Tyr
                 85                  90                  95

Glu Asp Gly Gly Tyr Leu Thr Ile His Gln Asp Thr Ser Ile Gln Gly
            100                 105                 110

Asp Ser Phe Ile Phe Lys Val Lys Val Ile Gly Ala Asn Phe Pro Ala
        115                 120                 125

Asn Gly Pro Val Met Gln Lys Lys Thr Ala Gly Trp Glu Pro Cys Val
    130                 135                 140
```

```
Glu Met Leu Tyr Pro Arg Asp Gly Val Leu Cys Gly Gln Ser Leu Met
145                 150                 155                 160

Ala Leu Lys Cys Thr Asp Gly Asn His Leu Thr Ser His Leu Arg Thr
            165                 170                 175

Thr Tyr Arg Ser Arg Lys Pro Ala Asn Ala Val Asn Met Pro Lys Phe
        180                 185                 190

His Phe Gly Asp His Arg Ile Glu Ile Leu Lys Glu Ala Glu Pro Gly
    195                 200                 205

Lys Phe Tyr Glu Gln Tyr Glu Ser Ala Val Ala Arg Tyr Cys Glu Ala
210                 215                 220

Ala Pro Ser Lys Leu Gly His His
225                 230

<210> SEQ ID NO 12
<211> LENGTH: 699
<212> TYPE: DNA
<213> ORGANISM: Actinia equina
<220> FEATURE:
<221> NAME/KEY: CDS
<222> LOCATION: (1)..(696)

<400> SEQUENCE: 12
```

| | | | | | | | | | | | | | | | | |
|---|---|---|---|---|---|---|---|---|---|---|---|---|---|---|---|---|
| atg | tct | tca | ttg | gtt | aag | aag | gat | atg | tgc | atc | aag | atg | acc | atg | gaa | 48 |
| Met | Ser | Ser | Leu | Val | Lys | Lys | Asp | Met | Cys | Ile | Lys | Met | Thr | Met | Glu | |
| 1 | | | | 5 | | | | | 10 | | | | | 15 | | |
| ggg | aca | gta | aat | ggt | cac | cac | ttc | aag | tgt | gta | gga | gaa | gga | gaa | ggc | 96 |
| Gly | Thr | Val | Asn | Gly | His | His | Phe | Lys | Cys | Val | Gly | Glu | Gly | Glu | Gly | |
| | | | 20 | | | | | 25 | | | | | 30 | | | |
| aag | cca | ttt | gaa | ggt | acc | cag | gag | gaa | aag | ata | aga | atc | act | gaa | gga | 144 |
| Lys | Pro | Phe | Glu | Gly | Thr | Gln | Glu | Glu | Lys | Ile | Arg | Ile | Thr | Glu | Gly | |
| | | 35 | | | | | 40 | | | | | 45 | | | | |
| ggt | ccc | tta | cca | ttt | gcg | tac | gat | att | ttg | gca | cct | tgt | tgc | atg | tat | 192 |
| Gly | Pro | Leu | Pro | Phe | Ala | Tyr | Asp | Ile | Leu | Ala | Pro | Cys | Cys | Met | Tyr | |
| | 50 | | | | | 55 | | | | | 60 | | | | | |
| gga | agc | aaa | acc | ttc | atc | aag | cat | gtc | tca | ggg | att | cca | gat | tac | ttc | 240 |
| Gly | Ser | Lys | Thr | Phe | Ile | Lys | His | Val | Ser | Gly | Ile | Pro | Asp | Tyr | Phe | |
| 65 | | | | | 70 | | | | | 75 | | | | | 80 | |
| aag | gat | tct | tta | cct | gaa | gga | tac | act | tgg | gaa | aga | acc | caa | atc | tac | 288 |
| Lys | Asp | Ser | Leu | Pro | Glu | Gly | Tyr | Thr | Trp | Glu | Arg | Thr | Gln | Ile | Tyr | |
| | | | | 85 | | | | | 90 | | | | | 95 | | |
| gag | gat | gga | ggc | tat | ctt | acc | att | cac | cag | gac | aca | agc | ata | cag | gga | 336 |
| Glu | Asp | Gly | Gly | Tyr | Leu | Thr | Ile | His | Gln | Asp | Thr | Ser | Ile | Gln | Gly | |
| | | | 100 | | | | | 105 | | | | | 110 | | | |
| gat | agc | ttt | att | ttc | aag | gtt | aaa | gtc | atc | ggt | gcc | aac | ttc | cct | gcc | 384 |
| Asp | Ser | Phe | Ile | Phe | Lys | Val | Lys | Val | Ile | Gly | Ala | Asn | Phe | Pro | Ala | |
| | | 115 | | | | | 120 | | | | | 125 | | | | |
| aat | ggt | ccc | gtg | atg | cag | aag | aaa | aca | gcc | gga | tgg | gaa | cca | tgc | gta | 432 |
| Asn | Gly | Pro | Val | Met | Gln | Lys | Lys | Thr | Ala | Gly | Trp | Glu | Pro | Cys | Val | |
| | 130 | | | | | 135 | | | | | 140 | | | | | |
| gag | atg | ctt | tat | cca | cgt | gac | gga | gtc | ctg | tgt | ggg | cag | tcc | ttg | atg | 480 |
| Glu | Met | Leu | Tyr | Pro | Arg | Asp | Gly | Val | Leu | Cys | Gly | Gln | Ser | Leu | Met | |
| 145 | | | | | 150 | | | | | 155 | | | | | 160 | |
| gcc | ctg | aaa | tgc | act | gat | ggt | aac | cat | ttg | acg | agc | cat | ctg | cga | act | 528 |
| Ala | Leu | Lys | Cys | Thr | Asp | Gly | Asn | His | Leu | Thr | Ser | His | Leu | Arg | Thr | |
| | | | | 165 | | | | | 170 | | | | | 175 | | |
| act | tac | agg | tcc | aga | aag | cca | gcc | aat | gcg | gtt | aat | atg | cca | aaa | ttt | 576 |
| Thr | Tyr | Arg | Ser | Arg | Lys | Pro | Ala | Asn | Ala | Val | Asn | Met | Pro | Lys | Phe | |
| | | | 180 | | | | | 185 | | | | | 190 | | | |
| cat | ttt | gga | gac | cat | cgc | att | gag | ata | cta | aag | gaa | gca | gaa | cca | ggc | 624 |
| His | Phe | Gly | Asp | His | Arg | Ile | Glu | Ile | Leu | Lys | Glu | Ala | Glu | Pro | Gly | |

-continued

```
                 195                 200                 205
aag ttt tat gaa cag tac gaa tca gca gtg gcc agg tac tgt gaa gct    672
Lys Phe Tyr Glu Gln Tyr Glu Ser Ala Val Ala Arg Tyr Cys Glu Ala
    210                 215                 220 gca cca tca aag ctt gga cat cac taa                                699
Ala Pro Ser Lys Leu Gly His His
225                 230

<210> SEQ ID NO 13
<211> LENGTH: 224
<212> TYPE: PRT
<213> ORGANISM: Lobophytum crassum

<400> SEQUENCE: 13

Met Ser Val Ile Lys Gln Glu Met Lys Ile Lys Leu His Met Glu Gly
1               5                   10                  15

Asn Val Asn Gly His Ala Phe Val Ile Glu Gly Asp Gly Lys Gly Lys
            20                  25                  30

Pro Tyr Asp Gly Thr Gln Thr Leu Asn Leu Thr Val Lys Glu Gly Ala
        35                  40                  45

Pro Leu Pro Phe Ser Tyr Asp Ile Leu Thr Asn Ala Phe Gln Tyr Gly
    50                  55                  60

Asn Arg Ala Phe Thr Lys Tyr Pro Ala Asp Ile Pro Asp Tyr Phe Lys
65                  70                  75                  80

Gln Thr Phe Pro Glu Gly Tyr Ser Trp Glu Arg Thr Met Ser Tyr Glu
                85                  90                  95

Asp Asn Ala Ile Cys Asn Val Arg Ser Glu Ile Ser Met Glu Gly Asp
            100                 105                 110

Cys Phe Ile Tyr Lys Ile Arg Phe Asp Gly Lys Asn Phe Pro Pro Asn
        115                 120                 125

Gly Pro Val Met Gln Lys Lys Thr Leu Lys Trp Glu Pro Ser Thr Glu
    130                 135                 140

Met Met Tyr Val Arg Asp Gly Phe Leu Met Gly Asp Val Asn Met Ala
145                 150                 155                 160

Leu Leu Leu Glu Gly Gly Gly His His Arg Cys Asp Phe Lys Thr Ser
                165                 170                 175

Tyr Lys Ala Lys Lys Val Val Gln Leu Pro Asp Tyr His Tyr Val Asp
            180                 185                 190

His Arg Ile Glu Ile Leu Ser His Asp Arg Asp Tyr Ser Lys Val Lys
        195                 200                 205

Leu Tyr Glu Asn Ala Val Ala Arg Tyr Ser Leu Leu Pro Ser Gln Ala
    210                 215                 220

<210> SEQ ID NO 14
<211> LENGTH: 675
<212> TYPE: DNA
<213> ORGANISM: Lobophytum crassum
<220> FEATURE:
<221> NAME/KEY: CDS
<222> LOCATION: (1)..(672)

<400> SEQUENCE: 14 atg agt gtg att aaa caa gaa atg aag atc aag ctg cat atg gaa gga    48
Met Ser Val Ile Lys Gln Glu Met Lys Ile Lys Leu His Met Glu Gly
1               5                   10                  15 aat gta aac ggt cat gca ttt gtg att gaa gga gat gga aaa gga aag    96
Asn Val Asn Gly His Ala Phe Val Ile Glu Gly Asp Gly Lys Gly Lys
            20                  25                  30 cct tac gat ggg aca cag act tta aac ctg aca gtg aaa gaa ggc gca   144
Pro Tyr Asp Gly Thr Gln Thr Leu Asn Leu Thr Val Lys Glu Gly Ala
```

```
                Pro Tyr Asp Gly Thr Gln Thr Leu Asn Leu Thr Val Lys Glu Gly Ala
                             35                  40                  45 cct ctc cct ttt tct tac gac atc ttg aca aat gcg ttc cag tac gga        192
Pro Leu Pro Phe Ser Tyr Asp Ile Leu Thr Asn Ala Phe Gln Tyr Gly
         50                  55                  60 aat aga gca ttc act aaa tat cca gcc gat ata cca gac tat ttc aag        240
Asn Arg Ala Phe Thr Lys Tyr Pro Ala Asp Ile Pro Asp Tyr Phe Lys
 65                  70                  75                  80 cag acg ttt ccc gag ggg tat tca tgg gaa aga acc atg agt tat gaa        288
Gln Thr Phe Pro Glu Gly Tyr Ser Trp Glu Arg Thr Met Ser Tyr Glu
                 85                  90                  95 gac aac gcc att tgc aac gtg aga agc gag atc agc atg gaa ggc gac        336
Asp Asn Ala Ile Cys Asn Val Arg Ser Glu Ile Ser Met Glu Gly Asp
            100                 105                 110 tgc ttt atc tat aaa att cgg ttt gat ggc aag aac ttt ccc ccc aat        384
Cys Phe Ile Tyr Lys Ile Arg Phe Asp Gly Lys Asn Phe Pro Pro Asn
        115                 120                 125 ggt cca gtt atg cag aag aaa act ttg aag tgg gaa cca tcc act gag        432
Gly Pro Val Met Gln Lys Lys Thr Leu Lys Trp Glu Pro Ser Thr Glu
    130                 135                 140 atg atg tac gtg cgt gat ggg ttt ctg atg ggt gat gtt aac atg gct        480
Met Met Tyr Val Arg Asp Gly Phe Leu Met Gly Asp Val Asn Met Ala
145                 150                 155                 160 ctg ttg ctt gaa gga ggt ggc cat cac cga tgt gac ttc aaa act tcc        528
Leu Leu Leu Glu Gly Gly Gly His His Arg Cys Asp Phe Lys Thr Ser
                165                 170                 175 tac aaa gcg aaa aag gtt gtg cag ttg cca gat tat cac tat gtg gac        576
Tyr Lys Ala Lys Lys Val Val Gln Leu Pro Asp Tyr His Tyr Val Asp
            180                 185                 190 cat cgt atc gag atc ttg agc cat gac agg gat tac agc aaa gtc aag        624
His Arg Ile Glu Ile Leu Ser His Asp Arg Asp Tyr Ser Lys Val Lys
        195                 200                 205 ctg tat gag aat gcg gtt gct cgc tat tct ttg ctg cca agt cag gcc        672
Leu Tyr Glu Asn Ala Val Ala Arg Tyr Ser Leu Leu Pro Ser Gln Ala
    210                 215                 220 tag                                                                    675
```

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gaaggrtgyg tcaayggrca y                                                 21

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
acvggdccat ydgvaagaaa rtt                                               23

<210> SEQ ID NO 17
<211> LENGTH: 36
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(25)
<223> OTHER INFORMATION: inosine
<220> FEATURE:
<221> NAME/KEY: modified_base
<222> LOCATION: (29)..(30)
<223> OTHER INFORMATION: inosine
<220> FEATURE:
<221> NAME/KEY: modified_base
<222> LOCATION: (34)..(35)
<223> OTHER INFORMATION: inosine

<400> SEQUENCE: 17
ggccacgcgt cgactagtac gggnngggnn gggnng                              36

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccatcttcaa agagaaaaga cctttt                                         25

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggccacgcgt cgactagtac                                                20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
catgagttct tgaaatagtc aac                                            23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atggctcttt caaagcgagg tg                                             22

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 22 ggggatccg accatggctc tttcaaagcg aggtg                        35

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tagaaatgac ctttcatatg acattc                                 26

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tctgtttcca tattgaaagg ctg                                    23

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atggtgtctt attcaaagca aggcatcgca ca                          32

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cgggatccga ccatggtgtc ttattcaaag caaggcatcg caca             44

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tagaaatgac ctttcatatg acattc                                 26

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

```
tctgtttcca tattgaaagg ctg                                              23
```

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
atggtgtctt attcaaagca aggcatcgca ca                                    32
```

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
cgggatccga ccatggtgtc ttattcaaag caaggcatcg caca                       44
```

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

```
atggctcttt caaagcacgg tc                                               22
```

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

```
gggggatccg accatggctc tttcaaagca cggtc                                 35
```

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (21)
<223> OTHER INFORMATION: a, c, g, t, unknown or other

<400> SEQUENCE: 33

```
ggnwsbgtna ayggvcayda ntt                                              23
```

```
<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: inosine
<220> FEATURE:
<221> NAME/KEY: modified_base
<222> LOCATION: (15)
<223> OTHER INFORMATION: inosine
<220> FEATURE:
<221> NAME/KEY: modified_base
<222> LOCATION: (18)
<223> OTHER INFORMATION: inosine
<220> FEATURE:
<221> NAME/KEY: modified_base
<222> LOCATION: (21)
<223> OTHER INFORMATION: inosine

<400> SEQUENCE: 34
gtcntcttyt gcacnacngg nccatydgva ggaaa                            35

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccttgaaaat aaagctatct                                             20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ccctgtatgc ttgtgtcctg                                             20

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cccggatccg accatggtgt cttcattggt taagaa                           36

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: inosine
```

<400> SEQUENCE: 38
grraggnwsb gthaayggvc a        21

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aactggaaga attcgcggcc gcaggaa        27

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: inosine
<220> FEATURE:
<221> NAME/KEY: modified_base
<222> LOCATION: (15)
<223> OTHER INFORMATION: inosine
<220> FEATURE:
<221> NAME/KEY: modified_base
<222> LOCATION: (18)
<223> OTHER INFORMATION: inosine
<220> FEATURE:
<221> NAME/KEY: modified_base
<222> LOCATION: (21)
<223> OTHER INFORMATION: inosine

<400> SEQUENCE: 40
gtcntcttyt gcacnacngg nccatydgva ggaaa        35

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttgtcaagat atcgaaagcg aacggcagag        30

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggccacgcgt cgactagtac        20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
            oligonucleotide

<400> SEQUENCE: 43
cttctcacgt tgcaaatggc                                               20

<210> SEQ ID NO 44
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cccggatccg atgagtgtga ttacawcaga aatgaagatg gagc                    44
```